(12) United States Patent
Phillips

(10) Patent No.: US 9,351,966 B2
(45) Date of Patent: *May 31, 2016

(54) COMPOSITION COMPRISING A COMBINATION OF OMEPRAZOLE AND LANSOPRAZOLE, AND A BUFFERING AGENT, AND METHODS OF USING SAME

(71) Applicant: The Curators of the University of Missouri, Columbia, MO (US)

(72) Inventor: Jeffrey O. Phillips, Ashland, MO (US)

(73) Assignee: The Curators of the University of Missouri, Columbia, MO (US)

(*) Notice: Subject to any disclaimer, the term of this patent is extended or adjusted under 35 U.S.C. 154(b) by 0 days.

This patent is subject to a terminal disclaimer.

(21) Appl. No.: 14/490,531

(22) Filed: Sep. 18, 2014

(65) Prior Publication Data

US 2015/0057314 A1    Feb. 26, 2015

Related U.S. Application Data

(63) Continuation of application No. 13/551,310, filed on Jul. 17, 2012, which is a continuation of application No. 12/389,243, filed on Feb. 19, 2009, now Pat. No. 8,247,440.

(60) Provisional application No. 61/030,045, filed on Feb. 20, 2008.

(51) Int. Cl.
*A61K 31/4439* (2006.01)
*A61K 9/20* (2006.01)
*A61K 31/415* (2006.01)
*A61K 31/44* (2006.01)

(52) U.S. Cl.
CPC ........... *A61K 31/4439* (2013.01); *A61K 9/2009* (2013.01); *A61K 9/2054* (2013.01); *A61K 9/2059* (2013.01); *A61K 31/415* (2013.01); *A61K 31/44* (2013.01)

(58) Field of Classification Search
None
See application file for complete search history.

(56) References Cited

U.S. PATENT DOCUMENTS

| 5,620,964 | A | 4/1997 | Roth et al. |
| 5,840,737 | A | 11/1998 | Phillips |
| 6,489,346 | B1 | 12/2002 | Phillips |
| 6,645,988 | B2 | 11/2003 | Phillips |
| 6,699,885 | B2 | 3/2004 | Phillips |
| 6,780,882 | B2 | 8/2004 | Phillips |
| 7,020,505 | B1 | 3/2006 | Phillips |
| 7,317,937 | B2 | 1/2008 | Phillips |
| 7,399,772 | B2 | 7/2008 | Phillips |
| 2001/0016603 | A1* | 8/2001 | DeLuca ............... 514/557 |
| 2003/0118669 | A1 | 6/2003 | Phillips |
| 2003/0215527 | A1 | 11/2003 | Phillips |
| 2004/0048896 | A1 | 3/2004 | Phillips |
| 2004/0171646 | A1 | 9/2004 | Phillips |
| 2005/0004171 | A1 | 1/2005 | Phillips |
| 2005/0042304 | A1 | 2/2005 | Phillips |
| 2005/0054682 | A1 | 3/2005 | Phillips |
| 2005/0112193 | A1 | 5/2005 | Phillips et al. |
| 2005/0249806 | A1 | 11/2005 | Proehl et al. |
| 2006/0024238 | A1 | 2/2006 | Barth et al. |
| 2006/0276500 | A1 | 12/2006 | Phillips |
| 2007/0243251 | A1 | 10/2007 | Taneja et al. |
| 2007/0292498 | A1 | 12/2007 | Hall et al. |
| 2008/0031941 | A1 | 2/2008 | Pettersson et al. |
| 2008/0103169 | A1 | 5/2008 | Phillips |
| 2008/0275091 | A1 | 11/2008 | Phillips |
| 2009/0004269 | A1 | 1/2009 | Phillips |
| 2009/0022796 | A1 | 1/2009 | Phillips |
| 2009/0023771 | A1 | 1/2009 | Phillips |

FOREIGN PATENT DOCUMENTS

| CN | 101066251 | 7/2007 |
| WO | WO 03/009846 | 2/2003 |
| WO | WO 03/053221 | 7/2003 |
| WO | WO03053221 A2 * | 7/2003 |
| WO | WO 2006/116556 | 11/2006 |
| WO | WO 2006/116582 | 11/2006 |
| WO | WO2006116582 A2 * | 11/2006 |
| WO | WO 2008/057802 | 5/2008 |

OTHER PUBLICATIONS

Canadian Office Action for CA 2,726,367 dated Jan. 8, 2013.
Fleischer et al., "Endoscopic radiofrequency ablation for Barrett's esophagus: 5-year outcomes from a perspective multicenter trial," Endoscopy 2010; 42:781-789.
Fleischer et al., "Endoscopic ablation of Barrett's esophagus: a multicenter study with 2.5 year follow-up," Gastrointestinal endoscopy, vol. 68, Issue 5, pp. 867-876 (2008).
Ganz et al., "Circumferential ablation of Barrett's esophagus that contains high-grade dysplasia," vol. 68, Issue 1, pp. 35-40 (2008).
Gardner et al., "Determination of the reduction in gastric acidity necessary to prevent pathological oesephageal reflux in patients with gastro-oesophageal reflux disease treated with a proton pump inhibitor," Aliment Pharmacol Ther 2003, 17:955-964.
Kushner et al., "Review of Proton Pump Inhibitors for the Initial Treatment of Heartburn: Is There a Dose Ceiling Effect?" Adv Ther (2011) 28(5):367-388.
Sachs et al., "Novel Approaches to Inhibition of Gastric Acid Secretion," Curr Gastroenterol Rep (2010) 12:437-447.
Scarpignato et al., "Acid Suppression Therapy: Where do we go from here?" Dig Dis 2006:24:11-46.
Shaheen et al., Radiofrequency Ablation in Barrett's Esophagus with Dysplasia, N. Engl. J. Med 30; 22 pp. 2277-2288 (2009).

(Continued)

*Primary Examiner* — Melenie McCormick
*Assistant Examiner* — Taina D Matos Negron
(74) *Attorney, Agent, or Firm* — Perkins Coie LLP

(57) ABSTRACT

The present disclosure relates to pharmaceutical compositions comprising omeprazole, lansoprazole and sodium bicarbonate. Methods of using such compositions are also provided.

26 Claims, No Drawings

(56) References Cited

OTHER PUBLICATIONS

Sharma et al., "Balloon-based circumferential, endoscopic radiofrequency ablation of Barrett's esophagus; 1-year follow-up 100 patients," Gastrointestinal Endoscopy, vol. 65, issue 2, pp. 185-195 (2007).

Sharma et al., "Circumferential focal ablation of Barrett's esophagus containing dysplasia," The Amer. Journ. of Gastroenterology: official publication of the National Gastroenterological Assocation, vol. 104, Issue 2, pp. 310-317 (2009).

Shin et al., "Pharmacology of Proton Pump Inhibitors," Current Gastroenterology Reports 2008, 10:528-534.

Texas medicare DUR (drug utilization review) Proton Pump Inhibitors: Medical Drug Use Review Criteria for Outpatient Use (Developed Oct. 2000, revised, Dec. 2001, Oct. 2002, Nov. 2003, Dec. 2005, Jun. 2009, Sep. 2009).

Yang et al., "Long-term Proton Pump Inhibitor Therapy and Risk of Hip Fracture," JAMA, vol. 296 (24), pp. 2947-2953 (2006).

YE Chinese Application Publication No. CN 11066251 published Nov. 7, 2007 certified translation by Park IP.

Supplementary European Search Report for European Patent Application No. EP097102577 dated Mar. 31, 2011.

Vippagunta et al., Advanced Drug Delivery Reviews, 48 (2001) pp. 3-26.

* cited by examiner

COMPOSITION COMPRISING A COMBINATION OF OMEPRAZOLE AND LANSOPRAZOLE, AND A BUFFERING AGENT, AND METHODS OF USING SAME

This application claims priority to and the benefit as a continuation application of U.S. patent application entitled, "COMPOSITION COMPRISING A COMBINATION OF OMEPRAZOLE AND LANSOPRAZOLE, AND A BUFFERING AGENT, AND METHODS OF USING SAME," Ser. No. 13/551,310 filed Jul. 17, 2012, which is a continuation of U.S. patent application entitled, "COMPOSITION COMPRISING OMEPRAZOLE, LANSOPRAZOLE AND AT LEAST ONE BUFFERING AGENT," Ser. No. 12/389,243, filed Feb. 19, 2009 (now U.S. Pat. No. 8,247,440), which claims the benefit of priority to U.S. Provisional application entitled, "COMPOSITIONS COMPRISING OMEPRAZOLE, LANSOPRAZOLE, AND A BUFFERING AGENT AND METHODS OF USING SAME," Ser. No. 61/030,045, filed Feb. 20, 2008, the entirety of their contents of which are incorporated herein by reference and relied upon. Described herein are pharmaceutical compositions comprising omeprazole, lansoprazole and buffering agent. Methods of using such compositions are also provided.

FIELD OF THE INVENTION

Described herein are pharmaceutical compositions comprising omeprazole, lansoprazole and buffering agent. Methods of using such compositions are also provided.

BACKGROUND

As used herein, the phrase "acid labile pharmaceutical agent" refers to any pharmacologically active drug subject to acid-catalyzed degradation. One class of acid labile pharmaceutical agents is a class of antisecretory agents that do not exhibit anticholinergic or $H_2$ histamine antagonistic properties, but that suppress gastric acid secretion by the specific inhibition of the $H^+$, $K^+$-ATPase enzyme system at the secretory surface of the gastric parietal cell (hereinafter "proton pump inhibitors" or "PPIs"). These agents provide a more specific class of inhibitors of gastric acid secretion in mammals, such as humans, by blocking the final step of acid production.

One particular class of PPIs includes substituted benzimidazole compounds that contain a sulfinyl group bridging substituted benzimidazole and pyridine rings. Another class of PPIs is the class of substituted aryl-imidazoles, such as substituted bicyclic aryl-imidazoles. The mechanism of action of the PPIs occurs when they reach parietal cells from the blood and diffuse into the secretory canaliculi, where they become protonated and thereby trapped. The protonated agent is then believed to rearrange to form a sulfenic acid and a sulfenamide. The sulfenamide, in turn, is thought to interact covalently with sulfhydryl groups at critical sites in the extracellular (luminal) domain of the membrane-spanning $H^+$, $K^+$-ATPase. See e.g. Hardman et al., *Goodman & Gilman's The Pharmacological Basis of Therapeutics*, p. 907, 9$^{th}$ ed. (1996).

Currently available PPI medications have a delay in reaching maximal effect (for example, maintaining a gastric pH above about 3.5) such that it can take approximately five days to reach a steady state effect. Therefore, it would be desirable to have a significant effect on gastric pH before 5 days, beginning with the first dose of the medication.

SUMMARY

In various embodiments, the present disclosure provides pharmaceutical compositions comprising a first proton pump inhibitor (PPI1), having a therapeutically effective portion, which is optionally enteric coated; a subsequent proton pump inhibitor (PPI2), having a therapeutically effective portion, which is optionally enteric coated; and one or more buffering agents.

Another embodiment discloses a pharmaceutical composition comprising omeprazole, having a therapeutically effective portion which is optionally enteric coated, lansoprazole, having a therapeutically effective portion which is optionally enteric coated, and sodium bicarbonate or other buffering agents.

Methods of using such compositions for treating a patient, including patients with or without gastroparesis (slow stomach emptying), in need of therapy for various diseases and disorders, including gastric acid related disorders such as, but not limited to, severe erosive esophagitis (Los Angeles classification grade C & D), Barrett's esophagus and reversal of Barrett's esophagus, treatment to stop progression and encourage reversal of reflux-related esophageal metaplasia with low or high grade dysplasia, treatment to stop progression and encourage reversal of reflux related adenocarcinoma of the esophagus or acid-related adenocarcinoma of the stomach, treatment of patients undergoing ablation in Barrett's esophagus to prevent recurrence, duodenal ulcer, gastric ulcer, gastric and duodenal erosions and ulcerations, acid dyspepia, gastroesophageal reflux disease (GERD), poorly responsive symptomatic GERD, acid reflux, esophageal ulcers and erosions, precancerous and cancerous lesions of the esophagus induced by acid exposure, radiation or chemotherapy-induced esophagitis, acid hypersecretory conditions, gastrointestinal pathological hypersecretory conditions (such as Zollinger Ellison Syndrome), non-ulcer dyspepsia, short-term eradication of *Helicobacter pylori* (*H. pylori*) (less than 5 days treatment with 2 antibiotics chosen from the following group, but are not limited to, antibiotic penicillins (e.g. amoxicillin, benzylpenicillin, piperacillin, mecillinam, etc.), antibiotic cefems or cephalosporins (e.g. cefixime, cefuroxime, cefuroxime axetil, cefaclor, ceftizoxime, cefotaxime, ceftazidime, etc.), antibiotic macrolides (e.g. erythromycin, clarithromycin, azithromycin, telithromycin, roxithromycin, etc.), antibiotic tetracylines (e.g. tetracyline, minocycline, doxycycline, tigecycline, etc.), antibiotic aminoglycosides (e.g. gentamicin, kanamycin, netilmicin, amikacin, tobramycin, etc.), antibiotic carbapenems (e.g. imipenem, meropenem, doripenem, etc.), carbapenem ester type prodrug (e.g. tebipenem pivoxil, faropenem daloxate; other oral carbapenem prodrugs include GV-118819, CS-834, L-084, DZ-2649, CL-191121, etc.), antibiotic quinolones (e.g. norfloxacin, ofloxacin, levofloxacin, ciprofloxacin, sitafloxacin, clinafloxacin, gatifloxacin, moxifloxacin, pazufloxacin, prulifloxacin, olamufloxacin, ganefloxacin, gemifloxacin, trovafloxacin, etc.), antibiotic nitroimidazoles (e.g. metronidazole, tinidazole), and antibiotic rifamycin or ansamycin analogues (e.g. rifabutin, rifampicin, rifampin, rifaximin, rifalazil, and ryfamycin derivatives such as 3'-hydroxy-5'-(4-propylpiperazinyl)benzoxazinorifamycin)), extraesophageal or atypical manifestations of gastroesophageal reflux disease (such as but not limited to eye pain, asthma, bronchitis, pneumonia, chest pain, cough, recurrent laryngitis, globus pharyngeus, sinusitis, otalgia, otitis media, eustachian tube dysfunction, voice change, globus sensation, throat clearing, halitosis, sore throat, aphthous ulcers), nocturnal acid breakthrough (NAB), sleep apnea, sleep disturbance, stopping of gastrointestinal bleeding and prevention of rebleeding after gastrointestinal bleeding, pretreatment prior to endoscopic evaluation of upper GI bleeding, stress ulcer prevention, treatment of stress-related bleeding, seizure or apparent seizure activity, Sandifer's syndrome, failure to thrive, anorexia, anorexia nervosa, weight loss, apnea, and bradycardia are provided.

Other objects, features and advantages will be set forth in the Detailed Description that follows, and in part will be apparent from the description or may be learned by practice of the embodiments disclosed herein. These objects and advantages will be realized and attained by the processes and compositions particularly pointed out in the written description and claims hereof.

DETAILED DESCRIPTION

While the present invention is capable of being embodied in various forms, the description below of several embodiments is made with the understanding that the present disclosure is to be considered as an exemplification of the invention, and is not intended to limit the invention to the specific embodiments illustrated. Headings are provided for convenience only and are not to be construed to limit the invention in any way. Embodiments illustrated under any heading may be combined with embodiments illustrated under any other heading.

It has been discovered that a pharmaceutical composition comprising omeprazole and lansoprazole, can provide superior gastric acid inhibition than the use of a single type of proton pump inhibitor, with or without a buffering agent.

It is therefore provided herein a pharmaceutical composition comprising:
a) a first proton pump inhibitor (PPI1), having a therapeutically effective portion which is optionally enteric coated;
b) a second proton pump inhibitor (PPI2), having a therapeutically effective portion which is optionally enteric coated; and
c) one or more buffering agents.

It is also provided herein a pharmaceutical composition comprising:
a) omeprazole, having a therapeutically effective portion which is optionally enteric coated;
b) lansoprazole, having a therapeutically effective portion which is optionally enteric coated; and
c) sodium bicarbonate.

Methods of using such compositions for treating a patient, including patients with or without gastroparesis (slow stomach emptying), in need of therapy for various diseases and disorders, including gastric acid related disorders such as, but not limited to, severe erosive esophagitis (Los Angeles classification grade C & D), Barrett's esophagus and reversal of Barrett's esophagus, treatment to stop progression and encourage reversal of reflux-related esophageal metaplasia with low or high grade dysplasia, treatment to stop progression and encourage reversal of reflux related adenocarcinoma of the esophagus or acid-related adenocarcinoma of the stomach, treatment of patients undergoing ablation in Barrett's esophagus to prevent recurrence, duodenal ulcer, gastric ulcer, gastric and duodenal erosions and ulcerations, acid dyspepia, gastroesophageal reflux disease (GERD), poorly responsive symptomatic GERD, acid reflux, esophageal ulcers and erosions, precancerous and cancerous lesions of the esophagus induced by acid exposure, radiation or chemotherapy-induced esophagitis, acid hypersecretory conditions, gastrointestinal pathological hypersecretory conditions (such as Zollinger Ellison Syndrome), non-ulcer dyspepsia, short-term eradication of *H. pylori* (less than 5 days treatment with 2 antibiotics chosen from the following group, but are not limited to, antibiotic penicillins (e.g. amoxicillin, benzylpenicillin, piperacillin, mecillinam, etc.), antibiotic cefems or cephalosporins (e.g. cefixime, cefuroxime, cefuroxime axetil, cefaclor, ceftizoxime, cefotaxime, ceftazidime, etc.), antibiotic macrolides (e.g. erythromycin, clarithromycin, azithromycin, telithromycin, roxithromycin, etc.), antibiotic tetracylines (e.g. tetracyline, minocycline, doxycycline, tigecycline, etc.), antibiotic aminoglycosides (e.g. gentamicin, kanamycin, netilmicin, amikacin, tobramycin, etc.), antibiotic carbapenems (e.g. imipenem, meropenem, doripenem, etc.), carbapenem ester type prodrug (e.g. tebipenem pivoxil, faropenem daloxate; other oral carbapenem prodrugs include GV-118819, CS-834, L-084, DZ-2649, CL-191121, etc.), antibiotic quinolones (e.g. norfloxacin, ofloxacin, levofloxacin, ciprofloxacin, sitafloxacin, clinafloxacin, gatifloxacin, moxifloxacin, pazufloxacin, prulifloxacin, olamufloxacin, ganefloxacin, gemifloxacin, trovafloxacin, etc.), antibiotic nitroimidazoles (e.g. metronidazole, tinidazole), and antibiotic rifamycin or ansamycin analogues (e.g. rifabutin, rifampicin, rifampin, rifaximin, rifalazil, and ryfamycin derivatives such as 3'-hydroxy-5'-(4-propylpiperazinyl)benzoxazinorifamycin)), extraesophageal or atypical manifestations of gastroesophageal reflux disease (such as but not limited to eye pain, asthma, bronchitis, pneumonia, chest pain, cough, recurrent laryngitis, globus pharyngeus, sinusitis, otalgia, otitis media, eustachian tube dysfunction, voice change, globus sensation, throat clearing, halitosis, sore throat, aphthous ulcers), nocturnal acid breakthrough (NAB), sleep apnea, sleep disturbance, stopping of gastrointestinal bleeding and prevention of rebleeding after gastrointestinal bleeding, pretreatment prior to endoscopic evaluation of upper GI bleeding, stress ulcer prevention, treatment of stress-related bleeding, seizure or apparent seizure activity, Sandifer's syndrome, failure to thrive, anorexia, anorexia nervosa, weight loss, apnea, and bradycardia are provided.

Proton Pump Inhibitors

Compositions of the disclosure comprise at least one pharmaceutically acceptable acid labile pharmaceutical agent. For example, embodiments disclosed herein comprise at least one $H^+$, $K^+$-ATPase proton pump inhibitor (PPI). The term proton pump inhibitor or PPI means any acid labile pharmaceutical agent possessing pharmacological activity as an inhibitor of $H^+$, $K^+$-ATPase. Classes of PPIs include but are not limited to: substituted aryl-imidazoles, substituted bicyclic aryl-imidazoles, substituted benzimidazole compounds, and substituted imidazopyridines.

A PPI can, if desired, be in any form such as a free base, free acid, salt, ester, hydrate, anhydrate, salt hydrate, amide, enantiomer, isomer, tautomer, prodrug, polymorph, derivative, or the like, provided that the free base, free acid, salt, ester, hydrate, anhydrate, salt hydrate, amide, enantiomer, isomer, tautomer, prodrug, polymorph, or any other pharmacologically suitable derivative is therapeutically active or undergoes conversion within or outside of the body to a therapeutically active form.

In one embodiment, illustrative PPIs are those compounds of Formula (A):

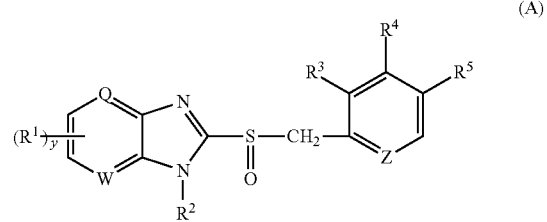

wherein

R¹ is hydrogen, alkyl, halogen, cyano, carboxy, carboalkoxy, carboalkoxyalkyl, carbamoyl, carbamoylalkyl, hydroxy, alkoxy which is optionally fluorinated, hydroxyalkyl, trifluoromethyl, acyl, carbamoyloxy, nitro, acyloxy, aryl, aryloxy, alkylthio, or alkylsulfinyl;

R² is hydrogen, alkyl, acyl, acyloxy, alkoxy, amino, aralkyl, carboalkoxy, carbamoyl, alkylcarbamoyl, dialkylcarbamoyl, alkylcarbonylmethyl, alkoxycarbonylmethyl, or alkylsulfonyl;

R³ and R⁵ are the same or different and each is hydrogen, alkyl, $C_{1-4}$ lower alkyl (e.g. methyl, ethyl, etc.), alkoxy, amino, or alkoxyalkoxy;

R⁴ is hydrogen, alkyl, $C_{1-4}$ lower alkyl (e.g. methyl, ethyl, etc.), alkoxy which may optionally be fluorinated, or alkoxyalkoxy;

Q is nitrogen, CH, or CR¹;
W is nitrogen, CH, or CR¹;
y is an integer of 0 through 4; and
Z is nitrogen, CH, or CR¹;
or a free base, salt, ester, hydrate, salt hydrate, amide, enantiomer, isomer, tautomer, prodrug, polymorph, or derivative thereof.

One specific example of a PPI is tenatoprazole (TU-199, also called benatoprazole), or 5-methoxy-2-[[(4-methoxy-3,5-dimethyl-2-pyridyl)methyl]sulfinyl]imidazo[4,5-b]pyridine, described in EP 0254588, hereby incorporated by reference herein in its entirety. An alternative IUPAC name for tenatoprazole is 3-methoxy-8-[(4-methoxy-3,5-dimethyl-pyridin-2-yl)methyl sulfinyl]-2,7,9-triazabicyclo[4.3.0]nona-2,4,8,10-tetraene. Because of its relatively long elimination profile, tenatoprazole can be used for the treatment of conditions such as gastroesophageal reflux disease, gastrointestinal bleeding and dyspepsia, as described in the French patent application 0213113, hereby incorporated by reference herein in its entirety. Tenatoprazole is a proton pump inhibitor which is similar to the chemical structure of omeprazole (Merck Index No. 6913; CAS No. 73590-58-6), or 5-methoxy-2-[[(4-methoxy-3,5-dimethyl-2-pyridinyl) methyl]sulfinyl]-1H benzimidazole. Omeprazole is a widely used proton pump inhibitor of the class of substituted benzimidazoles. Tenatoprazole belongs to the class of substituted imidazopyridines and has an imidazo[4,5-b]pyridine moiety whereas omeprazole has a benzimidazole moiety.

Specific examples of suitable PPIs include esomeprazole (also referred to as S-omeprazole), ilaprazole (U.S. Pat. No. 5,703,097), tenatoprazole (or benatoprazole), omeprazole, lansoprazole, s-lansoprazole, rabeprazole, hydroxyomeprazole, pantoprazole, pariprazole, leminoprazole, dontoprazole, habeprazole, perprazole, ransoprazole, and nepaprazole, or a free base, a free acid, a salt, hydrate, ester, salt hydrate, amide, enantiomer, isomer, tautomer, polymorph, prodrug, or derivative of such compounds.

Other acid labile pharmaceutical agents include, but are not limited to: soraprazan (Altana); AZD-0865 (AstraZeneca); YH-1885 (PCT Publication WO 96/05177) (SB-641257) (2-pyrimidinamine, 4-(3,4-dihydro-1-methyl-2(1H)-isoquinolinyl)-N-(4-fluorophenyl)-5,6-dimethyl -monohydrochloride) (YuHan); BY-112 (Altana); SPI-447 (Imidazo[1,2-a]thieno(3,2-c)pyridin-3-amine,5-methyl-2-(2-methyl-3-thieny-1) (Shinnippon); 3-hydroxymethyl-2-methyl-9-phenyl-7H-8,9-dihydro-pyrano(2,-3-c)-imidazo[1,2-a] pyridine (PCT Publication WO 95/27714) (AstraZeneca); Pharmaprojects No. 4950 (3-hydroxymethyl-2-methyl-9-phenyl-7H8,9-dihydro -pyrano(2,3-c)-imidazo[1,2-a]pyridine) (AstraZeneca, ceased) WO 95/27714; Pharmaprojects No. 4891 (EP 700899) (Aventis); Pharmaprojects No. 4697 (PCT Publication WO 95/32959) (AstraZeneca); H-335/25 (AstraZeneca); T-330 (Saitama 335) (Pharmacological Research Lab); Pharmaprojects No. 3177 (Roche); BY-574 (Altana); Pharmaprojects No. 2870 (Pfizer); AU-1421 (EP 264883) (Merck); AU-2064 (Merck); AY-28200 (Wyeth); Pharmaprojects No. 2126 (Aventis); WY-26769 (Wyeth); pumaprazole (PCT Publication WO 96/05199) (Altana); YH-1238 (YuHan); Pharmaprojects No. 5648 (PCT Publication WO 97/32854) (Dainippon); BY-686 (Altana); YM-020 (Yamanouchi); GYKI-34655 (Ivax); FPL-65372 (Aventis); Pharmaprojects No. 3264 (EP 509974) (AstraZeneca); nepaprazole (To a Eiyo); HN-11203 (Nycomed Pharma); OPC-22575; pumilacidin A (BMS); saviprazole (EP 234485) (Aventis); SK and F-95601 (GSK, discontinued); Pharmaprojects No. 2522 (EP 204215) (Pfizer); S-3337 (Aventis); RS-13232A (Roche); AU-1363 (Merck); SK and F-96067 (EP 259174) (Altana); SUN 8176 (Daiichi Phama); Ro-18-5362 (Roche); ufiprazole (EP 74341) (AstraZeneca); and Bay-p-1455 (Bayer); or a free base, free acid, salt, hydrate, ester, salt hydrate, amide, enantiomer, isomer, tautomer, polymorph, prodrug, or derivative of such compounds.

Still other embodiments contemplated by the present disclosure include, but are not limited to those described in the following U.S. Pat. Nos. 4,628,098; 4,689,333; 4,786,505; 4,853,230; 4,965,269; 5,021,433; 5,026,560; 5,045,321; 5,093,132; 5,430,042; 5,433,959; 5,576,025; 5,639,478; 5,703,110; 5,705,517; 5,708,017; 5,731,006; 5,824,339; 5,840,737; 5,855,914; 5,879,708; 5,948,773; 6,017,560; 6,123,962; 6,187,340; 6,296,875; 6,319,904; 6,328,994; 4,255,431; 4,508,905; 4,636,499; 4,738,974; 5,690,960; 5,714,504; 5,753,265; 5,817,338; 6,093,734; 6,013,281; 6,136,344; 6,183,776; 6,328,994; 6,479,075; 6,489,346; 6,559,167; 6,645,988; 6,699,885; 7,101,573; 7,109,161.

Still other embodiments contemplated by the present disclosure include, but are not limited to those described in the following: EP 0254588; EP 0005129.

Other embodiments contemplated by the present disclosure include, but are not limited to those described in the following PCT Publications: WO 94/27988; WO 05/044223; WO 06/043280.

Still other embodiments contemplated by the present disclosure include, but are not limited to those described in the following U.S. Application Nos.: 20020192299; 20040131675; 20040146554; 20040248939; 20040248942; 20050003005; 20050031700; 20050037070; 20050054682; 20050112193; 20050220870; 20050222210; 20050239845; 20050244517; 20050249806; 20050249811; 20050266071; 20050288334; 20050277672; 20050277673; 20050277671; 20060024238; 20060134210; 20060147522; 20060159760; 20060167262; 20060173045; 20060204585.

The foregoing lists of suitable acid inhibitors are meant to be illustrative and not exhaustive as a person of ordinary skill in the art would recognize that there are many other suitable acid inhibitors that could be created.

Gastric acid inhibitors, including proton pump inhibitors as well as their salts, hydrates, esters, salt hydrates, amides, enantiomers, isomers, tautomers, polymorphs, prodrugs, and derivatives may be prepared using standard procedures that a person of ordinary skill in the art of synthetic organic chemistry would recognize. See, e.g., March, *Advanced Organic Chemistry: Reactions, Mechanisms and Structure,* 4th Ed. (New York: Wiley-Interscience, 1992); Leonard et al., *Advanced Practical Organic Chemistry* (1992); Howarth et al., *Core Organic Chemistry* (1998); and Weisermel et al., *Industrial Organic Chemistry* (2002).

"Pharmaceutically acceptable salts," or "salts," include the salt of a proton pump inhibitor prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic, methanesulfonic, ethanesulfonic, benzenesulfonic, pantothenic, toluenesulfonic, 2-hydroxyethanesulfonic, sulfanilic, cyclohexylaminosulfonic, algenic, beta-hydroxybutyric, galactaric and galacturonic acids.

In one embodiment, acid addition salts are prepared from the free base forms using, for example, methodologies involving reaction of the free base with a suitable acid. Suitable acids for preparing acid addition salts include both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like.

In other embodiments, an acid addition salt is reconverted to the free base by treatment with a suitable base. In a further embodiment, the acid addition salts of the proton pump inhibitors are halide salts, which are prepared, for example, using hydrochloric or hydrobromic acids. In still other embodiments, the basic salts are alkali metal salts, e.g., sodium salt.

Salt forms of proton pump inhibitors include, but are not limited to: a sodium salt form such as esomeprazole sodium, omeprazole sodium, tenatoprazole sodium, rabeprazole sodium, pantoprazole sodium; a magnesium salt form such as esomeprazole magnesium or omeprazole magnesium, described in U.S. Pat. No. 5,900,424; a calcium salt form; a potassium salt form such as the potassium salt of esomeprazole, described in U.S. Pat. No. 6,511,996; salt hydrate forms including but not limited to sodium hydrate salt forms, for example tenatoprazole sodium hydrate or omeprazole sodium hydrate. Other salts of esomeprazole are described in U.S. Pat. Nos. 4,738,974 and 6,369,085. Salt forms of pantoprazole and lansoprazole are discussed in U.S. Pat. Nos. 4,758,579 and 4,628,098, respectively.

The foregoing list of suitable salts of proton pump inhibitors is meant to be illustrative and not exhaustive as a person of ordinary skill in the art would recognize that other pharmaceutically acceptable salts of a proton pump inhibitor could be created.

In one embodiment, preparation of esters involves functionalizing hydroxyl and/or carboxyl groups that may be present within the molecular structure of the drug. In another embodiment, the esters are acyl-substituted derivatives of free alcohol groups, e.g., moieties derived from carboxylic acids of the formula $RCOOR_1$, where $R_1$ is a lower alkyl group. Esters can be reconverted to the free acids, if desired, by using procedures including but not limited to hydrogenolysis or hydrolysis.

"Amides" may be prepared using techniques known to those skilled in the art or described in the pertinent literature. For example, amides may be prepared from esters, using suitable amine reactants, or they may be prepared from an anhydride or an acid chloride by reaction with an amine group such as ammonia or a lower alkyl amine.

"Tautomers" of substituted bicyclic aryl-imidazoles include, e.g., tautomers of omeprazole, such as those described in U.S. Pat. Nos. 6,262,085; 6,262,086; 6,268,385; 6,312,723; 6,316,020; 6,326,384; 6,369,087; and 6,444,689.

An exemplary "isomer" of a substituted bicyclic aryl-imidazole is the isomer of omeprazole including, but not limited to, isomers described in: Oishi et al., Acta Cryst. (1989), C45, 1921-1923; U.S. Pat. No. 6,150,380; U.S. Patent Publication No. 02/0156284; and PCT Publication No. WO 02/085889.

Exemplary "polymorphs" include, but are not limited to, those described in PCT Publication No. WO 92/08716, and U.S. Pat. Nos. 4,045,563; 4,182,766; 4,508,905; 4,628,098; 4,636,499; 4,689,333; 4,758,579; 4,783,974; 4,786,505; 4,808,596; 4,853,230; 5,026,560; 5,013,743; 5,035,899; 5,045,321; 5,045,552; 5,093,132; 5,093,342; 5,433,959; 5,464,632; 5,536,735; 5,576,025; 5,599,794; 5,629,305; 5,639,478; 5,690,960; 5,703,110; 5,705,517; 5,714,504; 5,731,006; 5,879,708; 5,900,424; 5,948,773; 5,997,903; 6,017,560; 6,123,962; 6,147,103; 6,150,380; 6,166,213; 6,191,148; 5,187,340; 6,268,385; 6,262,086; 6,262,085; 6,296,875; 6,316,020; 6,328,994; 6,326,384; 6,369,085; 6,369,087; 6,380,234; 6,428,810; 6,444,689; and 6,462,0577.

In one embodiment, at least one proton pump inhibitor is not enteric coated. In another embodiment, a portion of at least one proton pump inhibitor is optionally enteric coated. In another embodiment, a therapeutically effective portion of at least one proton pump inhibitor is optionally enteric coated. In another embodiment, about 5%, about 15%, about 20%, about 30%, about 40%, about 50% or about 60% of at least one proton pump inhibitor is optionally enteric coated. In another embodiment, a portion of at least one proton pump inhibitor comprises a "thin enteric coat." The term "thin enteric coat" herein refers to a pH sensitive coating that is applied in a manner or amount such that it delays release of the coated substance in gastrointestinal fluid for a period of time, but ultimately allows release of some of the coated substance prior to passage into the duodenum.

In one embodiment, at least one proton pump inhibitor has a $D_{90}$, $D_{80}$, $D_{70}$ or $D_{50}$ particle size, by weight or by number, of less than about 900 μm, less than about 800 μm, less than about 700 μm, less than about 600 μm, less than about 500 μm, less than about 400 μm, less than about 300 μm, less than about 200 μm, less than about 150 μm, less than about 100 μm, less than about 80 μm, less than about 60 μm, less than about 40 μm, less than about 35 μm, less than about 30 μm, less than about 25 μm, less than about 20 μm, less than about 15 μm, less than about 10 μm, or less than about 5 μm.

In another embodiment, compositions are provided wherein a micronized proton pump inhibitor is of a size which allows greater than about 90%, greater than about 75%, or greater than about 50% of the proton pump inhibitor to be released from the dosage unit within about 1 hour, within about 50 minutes, within about 40 minutes, within about 30 minutes, within about 20 minutes, within about 10 minutes, or within about 5 minutes after placement in a standard dissolution test.

In still another embodiment, compositions of the disclosure comprise two PPIs in a total amount of about 1 mg to about 3000 mg, about 1 mg to about 2000 mg, about 1 mg to about 1000 mg, about 1 mg to about 750 mg, about 1 mg to about 500 mg, about 1 mg to about 300 mg, about 5 mg to about 250 mg, about 5 mg to about 200 mg, about 5 mg to about 175 mg, about 5 mg to about 120 mg, about 5 mg to about 100 mg, about 5 mg to about 80 mg, or about 5 mg to about 50 mg, for example about 5 mg, about 7.5 mg, about 10 mg, about 15 mg, about 20 mg, about 30 mg, about 40 mg, about 50 mg, about 60 mg, about 70 mg, about 80 mg, about 90 mg, about 100 mg, about 110 mg, about 120 mg, about 130 mg, about 140 mg, about 150 mg, about 160 mg, about 170 mg, about 180 mg, about 190 mg, or about 200 mg.

In still another embodiment, compositions of the disclosure comprise two PPIs where each is present in an amount of about 40 mg to about 160 mg, about 50 mg to about 150 mg, about 60 mg to about 140 mg, about 60 to about 130 mg, about 60 mg to about 120 mg, about 60 to about 110 mg, about 60 mg to about 100 mg, about 70 mg to about 100 mg, or about 80 to about 100 mg.

Buffering Agent

Compositions of the disclosure comprise one or more pharmaceutically acceptable buffering agents. Buffering agents useful in the present disclosure include agents possessing pharmacological activity as a weak or strong base. In one embodiment, the buffering agent, when formulated with or administered substantially simultaneous with a PPI, functions to raise the pH of gastrointestinal fluid and thereby to substantially prevent or inhibit acid degradation of the PPI by gastrointestinal fluid for a period of time.

In another embodiment, buffering agents useful in accordance with the present disclosure comprise, but are not limited to, a salt of a Group IA metal including, for example, a bicarbonate salt of a Group IA metal, a carbonate salt of a Group IA metal, an alkaline earth metal buffering agent, an amino acid, an alkaline salt of an amino acid, an aluminum buffering agent, a calcium buffering agent, a sodium buffering agent, or a magnesium buffering agent. Other suitable buffering agents include alkali (sodium and potassium) or alkaline earth (calcium and magnesium) carbonates, phosphates, bicarbonates, citrates, borates, acetates, phthalates, tartrates, succinates and the like, such as sodium or potassium phosphate, citrate, borate, acetate, bicarbonate and carbonate.

Non-limiting examples of suitable buffering agents include aluminum, magnesium hydroxide, aluminum hydroxide/magnesium hydroxide co-precipitate, aluminum hydroxide/sodium bicarbonate co-precipitate, calcium acetate, calcium bicarbonate, calcium borate, calcium carbonate, calcium bicarbonate, calcium citrate, calcium gluconate, calcium glycerophosphate, calcium hydroxide, calcium lactate, calcium phthalate, calcium phosphates (including Calcium dihydrogen phosphate, tricalcium phosphate and the like), calcium succinate, calcium tartrate, calcium formate, calcium propionate, dibasic sodium phosphate, dipotassium hydrogen phosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium hydroxide, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium bicarbonate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, and trometarnol. (Based in part upon the list provided in *The Merck Index*, Merck & Co. Rahway, N.J. (2001)). In addition, due to the ability of proteins or protein hydrolysates to react with stomach acids, they too can serve as buffering agents in the present embodiments. Furthermore, combinations or mixtures of the above mentioned buffering agents can be used in the pharmaceutical formulations described herein.

Buffering agents also include buffering agents or combinations of buffering agents that interact with HCl (or other acids in the environment of interest) faster than the proton pump inhibitor interacts with the same acids. When placed in a liquid phase such as water, these buffering agents produce and maintain a pH greater than the pKa of the proton pump inhibitor.

Buffering agents also include peptides, such as L-carnosine. In one embodiment, a composition of the disclosure comprises L-carnosine. Still another embodiment of the disclosure comprises L-carnosine in a ratio of greater than about 20 parts L-carnosine to about 1 part PPI. Other embodiments comprise L-carnosine and PPI in an amount of about 20:1, about 25:1, about 30:1, about 35:1, about 40:1, about 45:1, or about 50:1.

Other embodiments of the disclosure comprises a PPI, at least one buffering agent in an amount of about 20 parts to about 1 part PPI, and a protein component in an amount of about 20 parts to about 1 part PPI. For example, an embodiment of the disclosure comprises tenatoprazole, sodium bicarbonate in an amount of about 20 parts to about 1 part tenatoprazole, and L-carnosine in an amount of about 20 parts to about 1 part tenatoprazole. Another embodiment of the disclosure comprises about 40 mg tenatoprazole, about 1600 mg sodium bicarbonate, and about 1600 mg L-carnosine. Still another embodiment of the disclosure comprises about 40 mg tenatoprazole, about 1600 mg sodium bicarbonate and magnesium hydroxide, and about 1600 mg L-carnosine. Yet another embodiment of the disclosure comprises about 40 mg omeprazole, about 1600 mg sodium bicarbonate and magnesium hydroxide, and about 1600 mg L-carnosine.

Other embodiments of the disclosure comprise omeprazole, sodium bicarbonate in an amount of about 20 parts to about 1 part omeprazole, and L-carnosine in an amount of about 20 parts to about 1 part omeprazole. For example, an embodiment of the disclosure comprises about 40 mg omeprazole, about 1600 mg sodium bicarbonate, and about 1600 mg L-carnosine.

The foregoing list of suitable buffering agents is meant to be illustrative and not exhaustive as a person of ordinary skill in the art would recognize that other pharmaceutically acceptable buffering agents could be created.

In various other embodiments, the buffering agent is present in a total amount of about 0.1 mEq/mg to about 5 mEq/mg of the proton pump inhibitor, about 0.5 mEq/mg to about 3 mEq/mg of the proton pump inhibitor, about 0.6 mEq/mg to about 2.5 mEq/mg of the proton pump inhibitor, about 0.7 mEq/mg to about 2.0 mEq/mg of the proton pump inhibitor, about 0.8 mEq/mg to about 1.8 mEq/mg of the proton pump inhibitor, about 1.0 mEq/mg to about 1.5 mEq/mg of the proton pump inhibitor. In another embodiment, the buffering agent is present in an amount of about 0.5 mEq/mg of the proton pump inhibitor, about 0.75 mEq/mg of the proton pump inhibitor, or about 1 mEq/mg of the proton pump inhibitor on a dry weight basis.

In still another embodiment, one or more buffering agents are present in a total amount of about 0.5 mEq to about 160 mEq, about 1 mEq to about 150 mEq, about 10 mEq to about 150 mEq, about 10 mEq to about 75 mEq, about 10 mEq to about 60 mEq, or about 10 mEq to about 50 mEq. Illustratively, a composition of the disclosure can comprise about 1 mEq, about 5 mEq, about 10 mEq, about 15 mEq, about 20 mEq, about 25 mEq, about 30 mEq, about 35 mEq, about 40 mEq, about 45 mEq, about 50 mEq, about 60 mEq, about 70 mEq, about 80 mEq, about 90 mEq, about 100 mEq, about 110 mEq, about 120 mEq, about 130 mEq, about 140 mEq, about 150 mEq, or about 160 mEq of buffering agent.

In yet another embodiment, one or more buffering agents are present in a total amount of about 10 mEq, about 11 mEq, about 12 mEq, about 13 mEq, about 14 mEq, about 15 mEq, or at least about 16 mEq.

In another embodiment, one or more buffering agents and the mixture of the first and subsequent proton pump inhibitors are present in a weight ratio of about 5:1, about 7:1, about 10:1, about 20:1, greater than about 20:1, about 21:1, about 22:1, about 23:1, about 25:1, about 30:1, about 35:1, about 40:1, greater than about 40:1, about 45:1, about 53:3; about 11:1, about 28:3, about 28:5, about 23:3, about 26:1, about 27:2, or about 31:1.

In still another embodiment, PPI1, PPI2, and one or more buffering agents are present in a weight ratio of about 2:1:50, about 3:2:50, about 2:1:25, about 2:1:60, about 3:2:25, about 2:1:20, about 1:1:50, about 1:2:50, about 1:1:25, about 1:1:60, about 1:2:25, or about 1:1:20.

In another embodiment, the amount of buffering agent present in a composition of the disclosure ranges from about 100 to about 4000 mg, about 200 to about 3500 mg, about 300 to about 3000 mg, about 400 to about 2500 mg, or about 500 to about 2200 mg, about 600 to about 2000, or about 700 to about 1800 mg. In other embodiments, the amount of buffering agent present in a composition of the disclosure is about 100 mg, about 200 mgs, or about 300 mgs, or about 400 mgs, or about 500 mgs, or about 600 mgs, or about 700 mgs, or about 800 mgs, or about 900 mgs, or about 1000 mgs, or about 1100 mgs, or about 1200 mgs, or about 1300 mgs, or about 1400 mgs, or about 1500 mgs, or about 1600 mgs, or about 1700 mgs, or about 1800 mgs, or about 1900 mgs, or about 2000 mgs, or about 2100 mgs, or about 2200 mgs, or about 2300 mgs, or about 2400 mgs, or about 2500 mgs, or about 2600 mgs, or about 2700 mgs, or about 2800 mgs, or about 2900 mgs, or about 3000 mgs, or about 3200 mgs, about 3500 mgs, or about 4000 mgs.

In another embodiment, the amount of buffering agent present is an amount of about 100 mg to about 2000 mg, about 200 mg to about 1750 mg, about 300 mg to about 1500 mg, about 400 mg to about 1250 mg, or about 500 mg to about 1000 mg.

In another embodiment, the amount of buffering agent present is an amount of about 100 mg to about 500 mg, about 200 mg to 400 mg, about 300 mg to about 400 mg, about 100 mg to about 350 mg, about 100 mg to about 300 mg, about 100 mg to about 250 mg, or 100 mg to about 200 mg.

In another embodiment, one or more buffering agents are present in a composition of the disclosure in a total amount that is greater than 800 mg, for example about 920 mg or at least about 1000 mg.

In still another embodiment, the buffering agent and the mixture of PPI1 and PPI2 (hereinafter "proton pump inhibitor mixture") are present in a weight ratio greater than 20:1, not less than about 21:1, not less than about 22:1, not less than about 23:1, not less than about 24:1, not less than about 25:1, not less than about 26:1, not less than about 27:1, not less than about 28:1, not less than about 29:1, not less than about 30:1, not less than about 31:1, not less than about 32:1, not less than about 33:1, not less than about 34:1, not less than about 35:1, not less than about 36:1, not less than about 37:1, not less than about 38:1, not less than about 39:1, not less than about 40:1, not less than about 41:1, not less than about 42:1, not less than about 43:1, not less than about 44:1, not less than about 45:1, not less than about 46:1, not less than about 47:1, not less than about 48:1, not less than about 49:1, not less than about 50:1, not less than about 53:3; not less than about 11:1, not less than about 28:3, not less than about 21; 1, not less than about 28:5, not less than about 23:3, not less than about 26:1, not less than about 53:3, not less than about 27:2, or not less than about 31:1.

In yet another embodiment, a composition is provided that comprises a combination of at least two non-amino acid buffering agents, wherein the combination of at least two non-amino acid buffering agents comprises substantially no aluminum hydroxide-sodium bicarbonate co-precipitate. In a related embodiment, if such a composition comprises a poly[phosphoryl/sulfon]-ated carbohydrate, the weight ratio of poly[phosphoryl/sulfon]-ated carbohydrate to buffering agent is less than 1:5 (0.2), less than 1:10 (0.1) or less than 1:20 (0.05). Alternatively, the poly[phosphoryl/sulfon]-ated carbohydrate is present in the composition, if at all, in an amount less than 50 mg, less than 25 mg, less than 10 mg or less than 5 mg. In another embodiment, the composition contains no poly[phosphoryl/sulfon]-ated carbohydrate.

In other embodiments, if the pharmaceutical composition comprises an amino acid buffering agent, the total amount of amino acid buffering agent present in the pharmaceutical composition is less than about 5 mEq, or less than about 4 mEq, or less than about 3 mEq.

The phrase "amino acid buffering agent" as used herein includes, but is not limited to, amino acids, amino acid salts, and amino acid alkali salts including, for example: glycine, alanine, threonine, isoleucine, valine, phenylalanine, glutamic acid, asparagininic acid, lysine and/or lysine glutamic acid salt, glycine hydrochloride, L-alanine, DL-alanine, L-threonine, DL-threonine, L-isoleucine, L-valine, L-phenylalanine, L-glutamic acid, L-glutamic acid hydrochloride, L-glutamic acid sodium salt, L-asparaginic acid, L-asparaginic acid sodium salt, L-lysine and L-lysine-L-glutamic acid salt. The term "non-amino acid buffering agent" herein includes buffering agents as defined hereinabove but does not include amino acid buffering agents.

The foregoing list of amino acid buffering agents is meant to be illustrative and not exhaustive as a person of ordinary skill in the art would recognize that other pharmaceutically acceptable amino acid buffering agents could be created.

In another embodiment, a composition of the disclosure comprises at least one non-amino acid buffering agent wherein the non-amino acid buffering agent is present in the composition in a total amount greater than 800 mg. In a related embodiment, if such a composition comprises a poly[phosphoryl/sulfon]-ated carbohydrate, the weight ratio of poly[phosphoryl/sulfon]-ated carbohydrate to buffering agent is less than 1:5 (02), less than 1:10 (0.1) or less than 1:20 (0.05). Alternatively, the poly[phosphoryl/sulfon]-ated carbohydrate is present in the composition, if at all, in an amount less than 50 mg, less than 25 mg, less than 10 mg or less than 5 mg.

In still another embodiment, a composition is provided which comprises at least one buffering agent in a total amount of at least about 10 mEq. In a related embodiment, if an amino acid buffering agent is present in the composition, at least one of the following conditions is met: (1) the weight ratio of amino acid buffering agent:proton pump inhibitor mixture is greater than 20:1; (2) the composition comprises at least two non-amino acid buffering agents; (3) the composition comprises at least one non-amino acid buffering agent wherein the weight ratio of the at least one non-amino acid buffering agent:proton pump inhibitor mixture is greater than 20:1; and/or (4) the weight ratio of total buffering agent:proton pump inhibitor mixture is greater than 40:1.

In yet another embodiment, a composition is provided which comprises at least one buffering agent in a total amount of at least about 10 mEq. In a related embodiment, if an amino acid buffering agent is present in the composition, at least one of the following conditions is met: (1) the weight ratio of PPI1:PPI2:amino acid buffering agent is about 2:1:50, about 3:2:50, about 2:1:25, about 2:1:60, about 3:2:25, about 2:1:20, about 1:1:50, about 1:2:50, about 1:1:25, about 1:1:60, about 1:2:25, or about 1:1:20; (2) the composition comprises at least two non-amino acid buffering agents; (3) the composition comprises at least one non-amino acid buffering agent wherein the weight ratio of PPI1:PPI2:non-amino acid buffering agent is about 2:1:50, about 3:2:50, about 2:1:25, about 2:1:60, about 3:2:25, about 2:1:20, about 1:1:50, about 1:2:50, about 1:1:25, about 1:1:60, about 1:2:25, or about 1:1:20; and/or (4) the weight ratio of PPI1:PPI2:total buffering agent is about 2:1:50, about 3:2:50, about 2:1:25, about 2:1:60, about 3:2:25, about 2:1:20, about 1:1:50, about 1:2:50, about 1:1:25, about 1:1:60, about 1:2:25, or about 1:1:20.

In other embodiments, where two or more buffering agents are present, the two or more buffering agents comprise at least two non-amino acid buffering agents, wherein the combination of at least two non-amino acid buffering agents comprises substantially no aluminum hydroxide-sodium bicarbonate co-precipitate.

In still another embodiment, the buffering agent comprises a mixture of sodium bicarbonate, calcium carbonate, and magnesium hydroxide, wherein the sodium bicarbonate, calcium carbonate, and magnesium hydroxide are each present in an amount of about 0.1 mEq/mg proton pump inhibitor mixture to about 5 mEq/mg of the proton pump inhibitor mixture.

In another embodiment, the buffering agent comprises a mixture of sodium bicarbonate, calcium carbonate, and magnesium hydroxide, wherein the sodium bicarbonate, calcium carbonate, and magnesium hydroxide are each present in an amount of about 0.1 mEq/mg proton pump inhibitor to about 5 mEq/mg of the either proton pump inhibitor.

Also provided herein are pharmaceutical compositions comprising at least one soluble buffering agent. The term "soluble buffering agent" as used herein refers to an antacid that has a solubility of at least about 500 mg/mL, or at least about 300 mg/mL, or at least about 200 mg/mL, or at least about 100 mg/mL in gastrointestinal fluid or simulated gastrointestinal fluid.

In some embodiments, the buffering agent has a defined particle size distribution. For example, in one embodiment, the $D_{50}$, $D_{70}$, $D_{80}$, or $D_{90}$ particle size of the buffering agent, by weight or by number, is no greater than about 10 µm, is no greater than about 20 µm, no greater than about 30 µm, no greater than about 40 µm, no greater than about 50 µm, no greater than about 60 µm, no greater than about 70 µm, no greater than about 80 µm, no greater than about 90 µm, no greater than about 100 µm in diameter, no greater than about 200 µm in diameter, no greater than about 300 lam in diameter, no greater than about 400 µm in diameter, no greater than about 1000 µm in diameter, no greater than about 2000 µm in diameter, no greater than about 3000 µm in diameter, no greater than about 4000 µm in diameter, no greater than about 6000 µm in diameter, or no greater than about 9000 µm in diameter.

The foregoing list of suitable buffering agents is meant to be illustrative and not exhaustive as a person of ordinary skill in the art would recognize that other pharmaceutically acceptable buffering agents could be created.

NSAIDs and Aspirins

In one embodiment, compositions of the invention comprise an NSAID. The term "NSAID" as used herein refers to compounds acting as a non-steroidal anti-inflammatory agent as identified as such by one of ordinary skill in the art.

Illustratively, the Merck Manual, 16th Edition, Merck Research Laboratories (1990) pp 1308-1309 provides well known examples of NSAIDs. Exemplary NSAIDs include, but are not limited to, salicylates, indomethacin, flurbiprofen, diclofenac, ketorolac, naproxen, piroxicam, tebufelone, ibuprofen, etodolac, nabumetone, tenidap, alcofenac, antipyrine, aminopyrine, dipyrone, aminopyrone, phenylbutazone, clofezone, oxyphenbutazone, prexazone, apazone, benzydamine, bucolome, cinchopen, clonixin, ditrazol, epirizole, fenoprofen, floctafeninl, flufenamic acid, glaphenine, indoprofen, ketoprofen, meclofenamic acid, mefenamic acid, niflumic acid, phenacetin, salidifamides, sulindac, suprofen and tolmetin. The salicylates may include acetylsalicylic acid, sodium acetylsalicylic acid, calcium acetylsalicylic acid, salicylic acid, and sodium salicylate.

In one embodiment, an NSAID, if present, is present in a total amount of about 0.1% to about 85%, about 0.5% to about 75%, or about 1% to about 60%, by total weight of the composition. Illustratively, the NSAID can be present in an amount of about 1%, about 2% about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 46%, about 48%, about 49%, about 50%, about 51%, about 52%, about 53%, about 54%, about 55%, about 56%, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83% about 84%, or about 85%, by weight of the total composition.

In another embodiment, an NSAID, if present, is present in a total amount of about 1 mg to about 1500 mg, about 1 mg to about 1200 mg, about 1 mg to about 1000 mg, about 1 mg to about 800 mg or about 1 mg to about 500 mg.

In other embodiments, the NSAID is present in a composition of the invention in an amount of about 50 mg, about 100 mg, about 150 mg, about 200 mg, about 250 mg, about 300 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, or about 1200 mg.

In one embodiment, no portion of the NSAID is enteric coated. In another embodiment, at least a portion of the NSAID is not enteric coated. In another embodiment, at least a therapeutically effective portion of the NSAID is not enteric coated. In another embodiment, at least about 5%, about 15%, about 20%, about 30%, about 40%, about 50% or about 60% of the NSAID is not enteric coated. In another embodiment, a portion of the NSAID comprises a "thin enteric coat" as is defined above.

The term "pain" includes all types of pain, including, but not limited to, chronic pain, such as arthritis pain (e.g. pain associated with osteoarthritis and rheumatoid arthritis), neuropathic pain, post-operative pain, chronic lower back pain, cluster headaches, herpes neuralgia, phantom limb pain, central pain, dental pain, opioid-resistant pain, visceral pain, surgical pain, bone injury pain, pain during labor and delivery, pain resulting from burns, including sunburn, post partum pain, migraine, angina pain, and genitourinary tract-related pain including cystitis, the term also refers to nociceptive pain or nociception.

In other embodiments, the aspirin is present in a composition of the invention in an amount of about 50 mg to about 400 mg, about 60 mg to about 375 mg, about 70 mg to about 350 mg, about 80 mg to about 325 mg, about 90 to about 300 mg, or about 100 mg about 275 mg.

Pharmaceutical Excipients

Various embodiments can, if desired, include one or more pharmaceutically acceptable excipients. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition. Excipients include, by way of illustration and not limitation, diluents, disintegrants, binding agents, adhesives, wetting agents, lubricants, glidants, surface modifying agents, substances added to mask or counteract a disagreeable taste or odor, flavors, dyes, fragrances, and substances added to improve appearance of the composition. Any such excipients can be used in any dosage forms according to the present disclosure, including liquid, solid or semi-solid dosage forms.

Excipients optionally employed in various embodiments can be solids, semi-solids, liquids or combinations thereof. Compositions of the disclosure including excipients can be prepared by various pharmaceutical techniques such as admixing an excipient with a drug or therapeutic agent.

In various embodiments, compositions optionally comprise one or more pharmaceutically acceptable diluents as excipients. Suitable diluents illustratively include, without limitation, either individually or in combination, lactose, including anhydrous lactose and lactose monohydrate; starches, including directly compressible starch and hydrolyzed starches (e.g., Celutab™ and Emdex™); mannitol; sorbitol; xylitol; dextrose (e.g., Cerelose™ 2000) and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of α- and amorphous cellulose (e.g., Rexcel™) and powdered cellulose; calcium carbonate; glycine; bentonite; polyvinylpyrrolidone; and the like. Such diluents, if present, may constitute in total about 5% to about 99%, about 10% to about 85%, or about 20% to about 80%, of the total weight of the composition. In various embodiments, the diluent or diluents selected may exhibit suitable flow properties and, where tablets are desired, compressibility.

The use of extragranular microcrystalline cellulose (that is, microcrystalline cellulose added to a wet granulated composition after a drying step) can be used to alter or control hardness (for tablets) and/or disintegration time.

In various embodiments, compositions optionally comprise one or more pharmaceutically acceptable disintegrants as excipients, such as in tablet formulations. Suitable disintegrants include, without limitation, either individually or in combination, starches, including crosslinked polyvinylpyrrolidone (crospovidone USP/NF), carboxymethyl cellulose (sodium CMC), chitin, chitosan, sodium starch glycolate (e.g., Explotab™ of PenWest) and pregelatinized corn starches (e.g., National™ 1551, National™ 1550, and Colocorn™ 1500), clays (e.g., Veegum™ HV), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, and gums such as agar, guar, xanthan, locust bean, karaya, pectin and tragacanth gums.

Disintegrants may be added at any suitable step during the preparation of the composition, particularly prior to a granulation step or during a lubrication step prior to compression. Such disintegrants, if present, may constitute in total about 0.2% to about 30%, about 0.2% to about 10%, or about 0.2% to about 5%, of the total weight of the composition.

In one embodiment, crosslinked polyvinylpyrrolidone (crospovidone USP/NF) is an optional disintegrant for tablet or capsule disintegration, and, if present, may optionally constitute about 1% to about 5% of the total weight of the composition.

In another embodiment, chitin is an optional disintegrant for tablet or capsule disintegration.

In still another embodiment, chitosan is an optional disintegrant for tablet or capsule disintegration.

In still another embodiment, carboxymethyl cellulose (sodium CMC) is an optional disintegrant for tablet or capsule disintegration.

In another embodiment, croscarmellose sodium is a disintegrant for tablet or capsule disintegration, and, if present, may optionally constitute about 0.2% to about 10%, about 0.2% to about 7%, or about 0.2% to about 5%, of the total weight of the composition.

Various embodiments described herein optionally comprise one or more pharmaceutically acceptable binding agents or adhesives as excipients, particularly for tablet formulations. Such binding agents and adhesives may impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, without limitation, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, may constitute in total about 0.5% to about 25%, about 0.75% to about 15%, or about 1% to about 10%, of the total weight of the composition.

Compositions described herein optionally comprise one or more pharmaceutically acceptable wetting agents as excipients. Non-limiting examples of surfactants that can be used as wetting agents in various compositions include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefossé), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, may constitute in total about 0.25% to about 15%, about 0.4% to about 10%, or about 0.5% to about 5%, of the total weight of the composition.

Compositions described herein optionally comprise one or more pharmaceutically acceptable lubricants (including anti-adherents and/or glidants) as excipients. Suitable lubricants include, without limitation, either individually or in combination, glyceryl behapate (e.g., Compritol™ 888); stearic acid and salts thereof, including magnesium (magnesium stearate), calcium and sodium stearates; hydrogenated vegetable oils (e.g., Sterotex™); colloidal silica; talc; waxes; boric acid; sodium benzoate; sodium acetate; sodium fumarate; sodium chloride; DL-leucine; PEG (e.g., Carbowax™ 4000 and Carbowax™ 6000); sodium oleate; sodium lauryl sulfate; and magnesium lauryl sulfate. Such lubricants, if present, may constitute in total about 0.1% to about 10%, about 0.2% to about 8%, or about 0.25% to about 5%, of the total weight of the composition.

Suitable anti-adherents include, without limitation, talc, cornstarch, DL-leucine, sodium lauryl sulfate and metallic stearates. Talc is an anti-adherent or glidant used, for example, to reduce formulation sticking to equipment surfaces and also to reduce static in the blend. Talc, if present, may constitute about 0.1% to about 10%, about 0.25% to about 5%, or about 0.5% to about 2%, of the total weight of the composition.

Glidants can be used to promote powder flow of a solid formulation. Suitable glidants include, without limitation, colloidal silicon dioxide, starch, talc, tribasic calcium phosphate, powdered cellulose and magnesium trisilicate.

Compositions described herein can comprise one or more flavoring agents, sweetening agents, and/or colorants. Flavoring agents useful in the present embodiments include, without limitation, acacia syrup, alitame, anise, apple, aspartame, banana, Bavarian cream, berry, black currant, butter, butter pecan, butterscotch, calcium citrate, camphor, caramel, cherry, cherry cream, chocolate, cinnamon, citrus, citrus punch, citrus cream, cocoa, coffee, cola, cool cherry, cool citrus, cyclamate, cylamate, dextrose, eucalyptus, eugenol, fructose, fruit punch, ginger, glycyrrhetinate, glycyrrhiza (licorice) syrup, grape, grapefruit, honey, isomalt, lemon, lime, lemon cream, MagnaSweet®, maltol, mannitol, maple, menthol, mint, mint cream, mixed berry, nut, orange, peanut butter, pear, peppermint, peppermint cream, Prosweet® Powder, raspberry, root beer, rum, saccharin, safrole, sorbitol, spearmint, spearmint cream, strawberry, strawberry cream, stevia, sucralose, sucrose, Swiss cream, tagatose, tangerine, thaumatin, tutti fruitti, vanilla, walnut, watermelon, wild cherry, wintergreen, xylitol, and combinations thereof, for example, anise-menthol, cherry-anise, cinnamon-orange, cherry-cinnamon, chocolate-mint, honey-lemon, lemon-lime, lemon-mint, menthol-eucalyptus, orange-cream, vanilla-mint, etc.

Sweetening agents that can be used in the present embodiments include, by way of example and not limitation, acesulfame potassium (acesulfame K), alitame, aspartame, cyclamate, cylamate, dextrose, isomalt, MagnaSweet®, maltitol, mannitol, neohesperidine DC, neotame, Prosweet® Powder, saccharin, sorbitol, stevia, sucralose, sucrose, tagatose, thaumatin, xylitol, and the like.

The foregoing excipients can have multiple roles. For example, starch can serve as a filler as well as a disintegrant. The classification of excipients listed herein is not to be construed as limiting in any manner.

Pharmaceutical Dosage Forms

In various embodiments, compositions can be formulated as oral solid, liquid, or semi-solid dosage forms. In one embodiment, such compositions are in the form of discrete dose units or dosage units (e.g., tablet, capsule). The terms "dose unit" and/or "dosage unit" herein refer to a portion of a pharmaceutical composition that contains an amount of a therapeutic agent suitable for a single administration to provide a therapeutic effect. Such dosage units may be administered one to a small plurality (i.e. 1 to about 4) of times per day, or as many times as needed to elicit a therapeutic response. A particular dosage form can be selected to accommodate any desired frequency of administration to achieve a specified daily dose. Typically one dose unit, or a small plurality (i.e. up to about 4) of dose units, provides a sufficient amount of the active drug (e.g. at least one PPI) to result in the desired response or effect.

Alternatively, compositions of the disclosure can also be formulated for rectal, topical, or parenteral (e.g. subcutaneous, intramuscular, intravenous and intradermal or infusion) delivery.

In one embodiment, compositions of the disclosure are suitable for rapid onset of therapeutic effect, particularly with respect to the PPI components. In another embodiment, upon oral administration of a composition to a subject, at least a therapeutically effective amount of the PPIs is available for absorption by the subject. As discussed above, most commercially available PPIs require enteric coating to prevent exposure of the PPI to gastrointestinal fluids (and consequent drug degradation) by way of pH dependent coatings. Such coating, in turn, prevents rapid PPI absorption and therapeutic onset of action. Compositions of the present disclosure, by contrast, do not require enteric coating to maintain drug stability in gastrointestinal fluids and thereby provide for rapid absorption and onset of therapeutic effect. In fact, in one embodiment, a composition comprises at least a therapeutically effective amount of at least one PPI that is not enteric coated. However, other embodiments are compositions which optionally include at least part of one proton pump inhibitor that is enteric coated.

In another embodiment, a single dosage unit, be it solid or liquid, comprises a therapeutically and/or prophylactically effective amount of PPIs. The term "therapeutically effective amount" or "therapeutically and/or prophylactically effective amount" as used herein refers to an amount of compound or agent that is sufficient to elicit the required or desired therapeutic and/or prophylactic response, as the particular treatment context may require.

It will be understood that a therapeutically and/or prophylactically effective amount of a drug for a subject is dependent, inter alia, on the body weight of the subject. A "subject" herein to which a therapeutic agent or composition thereof can be administered includes a human subject of either sex and of any age, and also includes any nonhuman animal, particularly a domestic or companion animal, illustratively a cat, dog or a horse.

Solid Dosage Forms

In various embodiments, compositions of the disclosure are in the form of solid dosage forms or units. Non-limiting examples of suitable solid dosage forms include tablets (e.g. suspension tablets, bite suspension tablets, rapid dispersion tablets, chewable tablets, effervescent tablets, bilayer tablets, etc.), caplets, capsules (e.g. a soft or a hard gelatin capsule), powder (e.g. a packaged powder, a dispensable powder or an effervescent powder), lozenges, sachets, cachets, troches, pellets, granules, microgranules, encapsulated microgranules, powder aerosol formulations, or any other solid dosage form reasonably adapted for oral administration.

Tablets are an illustrative dosage form for compositions of the disclosure. Tablets can be prepared according to any technique used in the pharmaceutical industry. In one embodiment, tablets or other solid dosage forms can be prepared by processes that employ one or a combination of methods including, without limitation, (1) dry mixing, (2) direct compression, (3) milling, (4) dry or non-aqueous granulation, (5) wet granulation, or (6) fusion.

The individual steps in the wet granulation process of tablet preparation typically include milling and sieving of the ingredients, dry powder mixing, wet massing, granulation and final grinding. Dry granulation involves compressing a powder mixture into a rough tablet or "slug" on a heavy-duty rotary tablet press. The slugs are then broken up into granular particles by a grinding operation, usually by passage through an oscillation granulator. The individual steps include mixing of the powders, compressing (slugging) and grinding (slug reduction or granulation). Typically, no wet binder or moisture is involved in any of the steps.

In another embodiment, solid dosage forms such as tablets can be prepared by mixing PPI1 and PPI2 with at least one buffering agent as described herein above and, if desired, with one or more optional pharmaceutical excipient to form a substantially homogeneous preformulation blend. The preformulation blend can then be subdivided and optionally further processed (e.g. compressed, encapsulated, packaged, dispersed, etc.) into any desired dosage forms.

Compressed tablets can be prepared by compacting a powder or granulation composition of the disclosure. The term "compressed tablet" generally refers to a plain, uncoated tablet suitable for oral ingestion, prepared by a single compression or by pre-compaction tapping followed by a final compression. Tablets of the present disclosure may be coated or otherwise compounded to provide a dosage form affording the advantage of improved handling or storage characteristics. In one embodiment, such coating will be selected so as to not substantially delay onset of therapeutic effect of a composition upon administration to a subject. The term "suspension tablet" as used herein refers to a compressed tablet that rapidly disintegrates after placement in water.

In one embodiment, a composition comprises a multi-layer tablet having a core comprising two proton pump inhibitors; the core is substantially or completely surrounded by the buffering agent. The buffering agent layer can optionally be coated with one or more coating materials. In one embodiment, the optional coating is optionally an enteric coating. In a related embodiment, the buffering agent layer completely surrounds the core. In another embodiment, the buffering agent layer partially surrounds the core. In yet another embodiment, the buffering agent layer is in contact with a portion of or with all of the surface area of the core.

In another embodiment, a composition comprises a multi-layer tablet having a core comprising the first proton pump inhibitor. The core is substantially or completely surrounded by a second layer comprising a buffering agent. A third layer comprising the subsequent proton pump inhibitor substantially or completely surrounds the second layer comprising the buffering agent. The third layer is substantially or completely surrounded by a fourth layer comprising the same or different buffering agent. The fourth layer can optionally be coated with one or more coating materials. The successive layering of additional proton pump inhibitors and buffering agents can be continued for any number of iterations with the same or different proton pump inhibitors and buffering agents. In one embodiment, the optional coating is optionally an enteric coating. In a related embodiment, the second layer comprising buffering agent completely surrounds the core. In another embodiment, the second layer comprising buffering agent partially surrounds the core. In yet another embodiment, the second layer comprising buffering agent is in contact with a portion of or with all of the surface area of the core. In a related embodiment, the fourth layer comprising buffering agent completely surrounds the third layer comprising the subsequent proton pump inhibitor. In another embodiment, the fourth layer comprising buffering agent partially surrounds the third layer comprising the subsequent proton pump inhibitor. In yet another embodiment, the fourth layer comprising buffering agent is in contact with a portion of or with all of the third layer comprising the subsequent proton pump inhibitor.

In another embodiment, a composition comprises a multi-layer tablet having a core comprising either omeprazole or lansoprazole. The core is substantially or completely surrounded by a second layer comprising a buffering agent. A third layer comprising another form of PPI substantially or completely surrounds the second layer comprising the buffering agent. The third layer is substantially or completely surrounded by a fourth layer comprising the same or different buffering agent. The fourth layer can optionally be coated with one or more coating materials. The successive layering of additional forms proton pump inhibitors and buffering agents can be continued for any number of iterations with the same or different proton pump inhibitors and buffering agents. In one embodiment, the optional coating is optionally an enteric coating. In a related embodiment, the second layer comprising buffering agent completely surrounds the core. In another embodiment, the second layer comprising buffering agent partially surrounds the core. In yet another embodiment, the second layer comprising buffering agent is in contact with a portion of or with all of the surface area of the core. In a related embodiment, the fourth layer comprising buffering agent completely surrounds the third layer comprising the subsequent proton pump inhibitor. In another embodiment, the fourth layer comprising buffering agent partially surrounds the third layer comprising the subsequent proton pump inhibitor. In yet another embodiment, the fourth layer comprising buffering agent is in contact with a portion of or with all of the third layer comprising the subsequent proton pump inhibitor.

In still another embodiment, one or more intermediate layers exists in between the core and the buffering agent. The intermediate layers can comprise any pharmaceutically acceptable material, particularly inert and non-pH sensitive coating materials such as polymer based coatings.

In yet another embodiment, a composition comprises a multi-layer tablet having a core comprising a first PPI; the core is substantially or completely surrounded by the subsequent PPI and the buffering agent. Optionally, an intermediate layer can exist between the first PPI core and the subsequent PPI/buffering agent surrounding the core. In one embodiment, the optional intermediate layer is a coating layer. In another embodiment, the coating layer is optionally an enteric coating.

In another embodiment, a composition comprises a multi-layer tablet having a core comprising either omeprazole or lansoprazole; the core is substantially or completely surrounded by another form of PPI and the buffering agent. Optionally, an intermediate layer can exist between the omeprazole or lansoprazole core and the other PPI/buffering agent surrounding the core. In one embodiment, the optional intermediate layer is a coating layer. In another embodiment, the coating layer is optionally an enteric coating.

In one such embodiment, the buffering agent/PPI layer completely surrounds the core. In another embodiment, the buffering agent/PPI layer partially surrounds the core. In yet another embodiment, the buffering agent/PPI layer is in contact with a portion of or with all of the surface area of the core.

In another embodiment, compositions can be microencapsulated wherein the first PPI, subsequent PPI, and one or more buffering agents are microencapsulated together, for example as modified from the description in U.S. Patent Publication No. 2005/0037070, hereby incorporated by reference herein in its entirety.

In still another embodiment, compositions can be microencapsulated wherein the omeprazole, lansoprazole, and one or more buffering agents are microencapsulated together, for example as modified from the description in U.S. Patent Publication No. 2005/0037070, hereby incorporated by reference herein in its entirety.

In another embodiment, a composition comprises a first proton pump inhibitor, one or more additional proton pump inhibitors, and one or more buffering agents mixed together in powder form and optionally filled into a capsule, for example a hard or soft gelatin or HPMC capsule.

In another embodiment, a composition of the invention is in the form of a molded article, for example a pellet. The term "molded article" herein refers to a discrete dosage form that can be formed by compression, extrusion, or other similar processes. In one embodiment, the molded article is moldable. The term "moldable" in the present context means capable of being shaped or molded by hand. A moldable article herein will therefore have a hardness lower than a conventional pharmaceutical tablet. Such a moldable article will also be capable of being chewed by an animal, for example a horse.

Such an article can comprise, in addition to the PPI and buffering agent, and other excipients described herein, a filler, a sweetener and a flavoring agent. Extrusion is a process of shaping material by forcing it to flow through a shaped opening in a die or other solid. Extruded material emerges as an elongated article with substantially the same profile as the die opening.

In yet another embodiment, a composition comprises omeprazole, lansoprasole, and one or more buffering agents mixed together in powder form and optionally filled into a capsule, for example a hard or soft gelatin or HPMC capsule.

Liquid Dosage Forms

In another embodiment, compositions described herein can be in the form of liquid dosage forms or units. Non-limiting examples of suitable liquid dosage forms include solutions, suspension, elixirs, syrups, liquid aerosol formulations, etc.

In one embodiment, a liquid composition comprising water or other solvent, first PPI, one or more additional PPIs and a buffering agent can be prepared. In another embodiment, compositions described herein are in the form of a powder for suspension that can be suspended in a liquid vehicle prior to administration to a subject. While the powder for suspension itself, can be a solid dosage form of the present disclosure, the powder dispersed in liquid also comprises a liquid embodiment of the disclosure.

In another embodiment, a liquid composition comprising water or other solvent, omeprazole, lansoprazole and one or more buffering agents can be prepared. In another embodiment, compositions described herein are in the form of a powder for suspension that can be suspended in a liquid vehicle prior to administration to a subject. While the powder for suspension itself, can be a solid dosage form of the present disclosure, the powder dispersed in liquid also comprises a liquid embodiment of the disclosure.

Suspension compositions comprise a first PPI, one or more additional PPIs, one or more buffering agents, a liquid media (e.g. water, de-ionized water, etc.), and one or more optional pharmaceutical excipients. Such compositions, upon storage in a closed container maintained at either room temperature, refrigerated (e.g. about 5-10° C.) temperature, or freezing temperature for a period of about 1, 2, 3, 4, 5, 6, 7, 8, 9, 10, 11, or 12 months, exhibit about 90%, about 92.5%, about 95%, or about 97.5% of the original first PPI and/or the one or more additional PPIs present therein.

Other suspension compositions comprise omeprazole, lansoprazole, one or more buffering agents, a liquid media (e.g. water, de-ionized water, etc.), and one or more optional pharmaceutical excipients. Such compositions, upon storage in a closed container maintained at either room temperature, refrigerated (e.g. about 5-10° C.) temperature, or freezing temperature for a period of about 1, 2, 3, 4, 5, 6, 7, 8, 9, 10, 11, or 12 months, exhibit about 90%, about 92.5%, about 95%, or about 97.5% of the original omeprazole and/or the lansoprazole present therein.

Storage Stability

In one embodiment, compositions are in the form of a powder for suspension that is ultimately to be suspended in a liquid vehicle prior to administration to a subject. Liquid compositions comprising an acid labile PPI suspended in a liquid vehicle, without more, would typically exhibit relatively short periods of stability, even when maintained under refrigerated conditions. This is particularly inconvenient in the hospital setting as fresh batches of suspension are continually required. Suspension compositions of the disclosure are believed to exhibit improved storage stability.

Illustrative suspension compositions comprise a first PPI, one or more additional PPIs, at least one buffering agent, water, and one or more optional pharmaceutical excipients. Such compositions, upon storage in a closed container maintained at room temperature, refrigerated (e.g. about 5 to about 5-10° C.) temperature, or frozen for a period of about 1, 2, 3, 4, 5, 6, 7, 8, 9, 10, 11, or 12 months, may exhibit about 90%, about 92.5%, about 95%, or about 97.5% of the original first PPI and/or subsequent PPI present therein.

Administration and Bioavailability

In one embodiment, compositions of the disclosure are suitable for rapid onset of therapeutic effect, particularly with respect to the PPI components. In another embodiment, upon oral administration of a composition to a subject, at least a therapeutically effective amount of at least one PPI is available for absorption and metabolism by the subject. The phrase "available for absorption" in reference to an active ingredient such as a PPI means that the ingredient remains intact and in active form in the stomach for a sufficient amount of time to allow for absorption into the blood. As discussed above, most commercially available PPIs require enteric coating to prevent exposure of the PPI to gastrointestinal fluids (and consequent drug degradation) by way of pH dependent coatings. Such coating, in turn, prevents rapid PPI absorption and therapeutic onset of action. Compositions of the present disclosure, by contrast, do not require but can optionally include an enteric coating to maintain drug stability in gastrointestinal fluids and thereby provide for rapid absorption and onset of therapeutic effect. In fact, in one embodiment, a composition comprises at least a therapeutically effective amount of at least one PPI that is not enteric coated. Another embodiment provides for compositions having at least one PPI which is optionally enteric coated.

In another embodiment, upon oral administration of a composition described herein to a plurality of fasted adult human subjects, the subjects exhibit an average $T_{max}$ of active ingredient, (e.g. at least one PPI) within about 30 seconds to about 90 minutes, within about 1 minute to about 80 minutes, within about 5 minutes to about 60 minutes, within about 10 minutes to about 50 minutes, or within about 15 minutes to about 45 minutes.

In still another embodiment, upon administration of a composition described herein to a plurality of fasted adult human subjects, the subjects exhibit an average plasma concentration of at least one PPI of about 0.1 µg/ml, about 0.15 µg/ml, about 0.2 µg/ml, about 0.3 µg/ml, about 0.4 µg/ml, about 0.5 µg/ml, about 0.6 µg/ml, about 0.7 µg/ml, about 0.8 µg/ml, about 0.9 µg/ml, about 1 µg/ml, about 1.5 µg/ml, or about 2.0 µg/ml at any time within about 90 minutes, within about 75 minutes, within about 60 minutes, within about 55 minutes, within about 50 minutes, within about 45 minutes, within about 40 minutes, within about 35 minutes, within about 30 minutes, within about 25 minutes, within about 20 minutes, within about 17 minutes, within about 15 minutes, within about 12 minutes, or within about 10 minutes after administration.

In yet another embodiment, upon administration of a composition described herein to a plurality of fasted adult human subjects, the subjects exhibit a plasma concentration of active ingredient (e.g. at least one PPI) of about 0.1 µg/ml, about 0.15 µg/ml, about 0.2 µg/ml, about 0.3 µg/ml, about 0.4 µg/ml, about 0.5 µg/ml, about 0.6 µg/ml, about 0.7 µg/ml, about 0.8 µg/ml, about 0.9 µg/ml, about 1.0 µg/ml, about 1.5 µg/ml or about 2.0 µg/ml, maintained from about 15 minutes to about 60 minutes after administration, about 15 minutes after administration to about 90 minutes after administration, about 15 minutes to about 120 minutes after administration, or about 15 minutes to about 180 minutes after administration.

In another embodiment, upon administration of a composition described herein to a plurality of fasted adult human subjects, the subjects exhibit at least one of: a mean $C_{max}$ of PPI1 and/or PPI2 of about 500 µg/ml to about 2000 µg/ml, about 600 µg/ml to about 1900 µg/ml, or about 700 ng/ml to about 1800 µg/ml; a mean $T_{max}$ of PPI and/or PPI2 of about 0.15 to about 2 hours, about 0.25 to about 1.75 hours, or about 0.3 hours to about 1 hour; and/or a mean $AUC_{(0-inf)}$ of PPI and/or PPI2 of about 1000 to about 3000 µg*hr/ml, about 1500 to about 2700 µg*hr/ml, or about 1700 to about 2500 µg*hr/ml.

In another embodiment, upon administration of a composition described herein to a plurality of fasted adult human subjects, the subjects exhibit: a mean $C_{max}$ of PPI1 and/or PPI2 of about 500 µg/ml to about 2000 µg/ml, about 600 µg/ml to about 1900 µg/ml, or about 700 µg/ml to about 1800 µg/ml; a mean $T_{max}$ of PPI1 and/or PPI2 of about 0.15 to about 2 hours, about 0.25 to about 1.75 hours, or about 0.3 hours to about 1 hour; and a mean $AUC_{(0-inf)}$ of PPI1 and/or PPI2 of about 1000 to about 3000 µg*hr/ml, about 1500 to about 2700 µg*hr/ml, or about 1700 to about 2500 µg*hr/ml.

Parietal Cell Activators

In one embodiment, a composition of the present disclosure can further include one or more parietal cell activators. Parietal cell activators such as chocolate, calcium and sodium bicarbonate and other alkaline substances stimulate the parietal cells and enhance the pharmacologic activity of the PPI administered. For the purposes of this application, "parietal cell activator" or "activator" shall mean any compound or mixture of compounds possessing such stimulatory effect including, but not limited to, chocolate, sodium bicarbonate, calcium (for example, calcium carbonate, calcium bicarbonate, calcium gluconate, calcium hydroxide, calcium acetate and calcium glycerophosphate, calcium formate), peppermint oil, spearmint oil, coffee, tea and colas (even if decaffeinated), caffeine, theophylline, theobromine, and amino acids (particularly aromatic amino acids such as phenylalanine and tryptophan) and combinations thereof.

Parietal cell activators, if desired, are typically present in a composition of the disclosure in an amount sufficient to produce the desired stimulatory effect without causing untoward side effects to subjects. For example, chocolate, such as raw cocoa, is administered in an amount of about 5 mg to 2.5 g per 20 mg dose of omeprazole (or comparable pharmacologic dose of another proton pump inhibiting agent). The dose of activator administered to a subject, for example, a human, in the context of the present disclosure should be sufficient to result in enhanced effect of a PPI over a desired time frame.

Illustratively, the approximate effective ranges for various parietal cell activators per 20 mg dose of omeprazole (or comparable dose of other PPI) include, Chocolate (raw cocoa)—about 5 mg to about 2.5 g; Sodium bicarbonate—about 7 mEq to about 25 mEq; Calcium carbonate—about 1 mg to about 1.5 g; Calcium gluconate—about 1 mg to about 1.5 g; Calcium lactate—about 1 mg to about 1.5 g; Calcium hydroxide—about 1 mg to about 1.5 g; Calcium acetate—about 0.5 mg to about 1.5 g; Calcium glycerophosphate—about 0.5 mg to about 1.5 g; Peppermint oil—(powdered form) about 1 mg to about 1 g; Spearmint oil—(powdered form) about 1 mg to about 1 g; Coffee—about 20 ml to about 240 ml; Tea—about 20 ml to about 240 ml; Cola—about 20 ml to about 240 ml; Caffeine—about 0.5 mg to about 1.5 g; Theophylline—about 0.5 mg to about 1.5 g; Theobromine—about 0.5 mg to about 1.5 g; Phenylalanine—about 0.5 mg to about 1.5 g; and Tryptophan—about 0.5 mg to about 1.5 g.

Gastrointestinal Disorders

In various embodiments, the present disclosure provides for therapy of various diseases and disorders. Such diseases and disorders include, inter alia, gastrointestinal disorders and, in particular, acid related gastrointestinal disorders. The phrase "acid related gastrointestinal disorder" or "acid related gastrointestinal disease" refers generally to a disease or disorder that occurs due to an imbalance between acid and pepsin production on the one hand, so-called aggressive factors, and mucous, bicarbonate, and prostaglandin production on the other hand, so-called defensive factors.

The term "therapy" as used herein refers to treatment and/or prevention of a disorder or disease, such as a gastrointestinal disorder.

The term "treat" or "treatment" as used herein refers to any treatment of a disorder or disease, and includes, but is not limited to, preventing the disorder or disease from occurring in a subject that may be predisposed to the disorder or disease but has not yet been diagnosed as having the disorder or disease; inhibiting the disorder or disease, for example, arresting the development of the disorder or disease; relieving the disorder or disease, for example, causing regression of the disorder or disease; or relieving the condition caused by the disease or disorder, for example, stopping the symptoms of the disease or disorder.

The term "prevent" or "prevention," in relation to a disorder or disease, means preventing the onset of gastrointestinal disorder or disease development if none had occurred, or preventing further disorder or disease development if the disorder or disease was already present.

Compositions of the present disclosure can be in the form of an orally deliverable dosage unit. The terms "oral administration" or "orally deliverable" herein include any form of delivery of a therapeutic agent or a composition thereof to a subject wherein the agent or composition is placed in the mouth of the subject, whether or not the agent or composition is swallowed. Thus, "oral administration" includes buccal and sublingual as well as esophageal administration.

Chronic GERD can lead to Barrett's esophagus, dysplasia and eventually adenocarcinoma. (Devesa S S, et al., "Changing patterns in the incidence of esophageal and gastric carcinoma in the United States", Cancer Vol. 83, pp. 2049-53 (1998)) (National Cancer Institute's Surveillance, Epidemiology, and End Results program with age-adjustment using the 2000 U.S. standard population.). Indeed, "The incidence of adenocarcinoma of the esophagus is continuing to rise rapidly in the United States and Western Europe. We desperately need to detect these patients at an earlier stage AND find effective ways of preventing this disease. Attacking the progression of this disease in its earliest stage will be key to preventing the reflux-induced adenocarcinoma." Tom DeMeester and Parakrama Chandrasoma, "GERD; Reflux to Esophageal Adenocarcinoma", Academic Press (2006).

Sampliner has reported that extended treatment (years) with powerful PPI drugs, omeprazole and lansoprazole, given twice per day or more, only reversed Barrett's esophagus in 3 of 123 patients with Barrett's esophagus, with or without surgery. Sampliner, R., "Reduction of Acid Exposure and Regression of Barrett's Esophagus", Digestive Diseases, Vol. 18(4), pp. 203-207, (2000-2001).

Fackler, W., et al. investigated the therapeutic efficacy of the addition of a histamine 2 receptor antagonists ("H2RAs") to a PPI to block nocturnal acid breakthrough ("NAB") in 23 healthy volunteers and 20 GERD patients. Fackler, W., et al., Long-term Effect of $H_2RA$ Therapy on Nocturnal Gastric Acid Breakthrough", Gastroenterology, Vol. 122(3), pp. 625-632 (2002). All subjects then received 28 days of PPI (omeprazole 20 mg) plus H2RA (ranitidine 300 mg) nightly ("QHS") and monitored with an ambulatory pH monitor. The results of the study found that the combination of H2RA and PPI therapy reduced NAB only at the introduction of therapy. Due to H2RA tolerance, there was no difference in acid suppression between PPI twice daily and PPI twice daily+ H2RA after one week of combination therapy.

Spechler S J, et al. evaluated the effect of three times per day ("TID") dosing of esomeprazole on esophageal acidity in patients with Barrett's esophagus. It was found that despite the significant decrease in gastric acidity by high dose esomeprazole treatment, abnormal esophageal acid exposure continued in 16% to 23% of patients. Spechler, S., et al., "Gastric and Esophageal pH in Patients With Barrett's Esophagus Treated With Three Esomeprazole Dosages: A Randomized, Double-Blind, Crossover Trial", Am J Gastroenterol., Vol. 101, pp. 1964-1971 (2006). It is important to note that compliance with TID regimens is significantly lower than once daily regimens. Further, compliance continues to be reduced over time such that compliance at 14 days is higher than that at 30 or 60 days. To complicate this further it is recommended that the delayed release PPI medications he taken ½ hour prior to a meal to achieve optimal acid inhibition. Prior research has demonstrated that only 10% of patients comply with this recommendation. These studies illustrate that there is a need for a once daily treatment that can inhibit the esophageal acid sufficiently in patients with Barrett's esophagus such that a reversal of the Barrett's columnar esophagus can be achieved.

Compositions of the present disclosure can be employed to stop progression and encourage reversal of reflux-related esophageal metaplasia with low or high grade dysplasia. Compositions of the present disclosure can also be used to stop progression and encourage reversal of reflux related adenocarcinoma of the esophagus or acid-related adenocarcinoma of the stomach. In addition, compositions of the present disclosure can be used in the treatment of patients undergoing ablation in Barrett's esophagus to prevent recurrence. Compositions of the disclosure can further be used for treating a patient, including patients with or without gastroparesis (slow stomach emptying) and severe erosive esophagitis (Los Angeles classification grade C & D).

Non-steroidal anti-inflammatory Drugs (NSAIDs) are commonly used for their antiinflammatory, analgesic, and/or antipyretic effects. However, NSAIDs are known to have the potential to cause gastrointestinal (GI) bleeding and/or ulceration through a variety of mechanisms related to their topical and systemic effects. Once ulcerated, gastric acid in the stomach can cause painful irritation and upset stomach. Such GI bleeding and ulceration may depend on the length of the treatment as well as on the particular drug used. As a result, many subjects taking NSAIDs, particularly those subjects on chronic NSAID therapy, are at high risk of developing gastric ulcers.

Besides NSAID use, overproduction of gastric acid can also lead to gastric ulceration and other GI diseases and disorders. Moreover, overproduction of stomach acid can particularly irritate subjects with NSAID-related gastric irritation or ulceration.

Various diseases and disorders, including gastric acid related disorders such as, but not limited to, severe erosive esophagitis (Los Angeles classification grade C & D), Barrett's esophagus, reflux-related esophageal metaplasia with low or high grade dysplasia, related adenocarcinoma of the esophagus or acid-related adenocarcinoma of the stomach, duodenal ulcer, gastric ulcer, gastric and duodenal erosions and ulcerations, acid dyspepia, gastroesophageal reflux disease (GERD), poorly responsive symptomatic GERD, acid reflux, esophageal ulcers and erosions, precancerous and cancerous lesions of the esophagus induced by acid exposure, radiation or chemotherapy-induced esophagitis, acid hypersecretory conditions, gastrointestinal pathological hypersecretory conditions (such as Zollinger Ellison Syndrome), non-ulcer dyspepsia, *H. pylori* infection, extraesophageal or atypical manifestations of gastroesophageal reflux disease (such as but not limited to eye pain, asthma, bronchitis, pneumonia, chest pain, cough, recurrent laryngitis, globus pharyngeus, sinusitis, otalgia, otitis media, eustachian tube dysfunction, voice change, globus sensation, throat clearing, halitosis, sore throat, aphthous ulcers), nocturnal acid breakthrough (NAB), sleep apnea, sleep disturbance, stopping of gastrointestinal bleeding and prevention of rebleeding after gastrointestinal bleeding, pretreatment prior to endoscopic evaluation of upper GI bleeding, stress ulcer prevention, treatment of stress-related bleeding, seizure or apparent seizure activity, Sandifer's syndrome, failure to thrive, anorexia, anorexia nervosa, weight loss, apnea, and bradycardia.

The foregoing lists of disorders or diseases are meant to be illustrative and not exhaustive as a person of ordinary skill in the art would recognize that there are many other disorders or diseases to which the embodiments of the present disclosure could treat and/or prevent.

In one embodiment, compositions provide a method for treating and/or preventing a disorder or disease by administering a pharmaceutical composition comprising a first proton pump inhibitor, having a therapeutically effective portion which is optionally enteric coated, a second proton pump inhibitor, having a therapeutically effective portion which is optionally enteric coated, and at least one buffering agent, such as sodium bicarbonate.

In yet another embodiment, compositions provide a method for treating and/or preventing a disorder or disease by administering a pharmaceutical composition comprising omeprazole, having a therapeutically effective portion which is optionally enteric coated, lansoprazole, having a therapeutically effective portion which is optionally enteric coated, and sodium bicarbonate.

In another embodiment, compositions provide a method for treating and/or preventing a disorder or disease by administering a pharmaceutical composition comprising about 20 mg, about 30 mg, about 40 mg, about 50 mg, about 60 mg, about 70 mg, about 80 mg, about 90 mg, or about 100 mg omeprazole, having a therapeutically effective portion which is optionally enteric coated.

In another embodiment, compositions provide a method for treating and/or preventing a disorder or disease by administering a pharmaceutical composition comprising about 20 mg, about 30 mg, about 40 mg, about 50 mg, about 60 mg, about 70 mg, about 80 mg, about 90 mg, or about 100 mg omeprazole, having a therapeutically effective portion which is optionally enteric coated, about 20 mg, about 30 mg, about 40 mg, about 50 mg, about 60 mg, about 70 mg, about 80 mg, about 90 mg, or about 100 mg lansoprazole, having a therapeutically effective portion which is optionally enteric coated, and sodium bicarbonate in an amount of about 100 mg to about 2500 mg sodium bicarbonate.

In another embodiment, either or both PPIs could be enteric coated as tablets.

In various embodiments, the acid labile pharmaceutical agents can be mixed together and then enteric-coated as granules.

In still another embodiment, tenatoprazole can be enteric coated as granules and the other one or more proton pump inhibitors could be enteric coated as granules.

Integrated Gastric Acidity

Integrated gastric acidity (hereinafter "IGA") is a sensitive measure of gastric acid inhibition. It is calculated as the cumulative time-weighted average of the gastric acid concentration. IGA is sensitive to the change from baseline for gastric acidity, whereas mean or median gastric pH has low sensitivity in detecting change (i.e., drug induced) from baseline. IGA or intragastric acidity can be expressed as mmol·h/L. For example, the following values were found for IGA after a single dose of PPI is administered (i.e., Day 1). See Sercombe W. J., et al., "A placebo-controlled trial to assess the effects of 8 days of dosing with raberprazole vs. omeprazole on 24-hour intragastric acidity and gastrin concentration in young health male subjects", Aliment Pharmacol. Ther., Vol. 12, pp. 1079-1089 (1998).

|  | Placebo | Rabeprazole 20 mg delayed release | Omeprazole 20 mg delayed release |
| --- | --- | --- | --- |
| IGA-24$_{Day\,1}$ | 997 mmol · h/L | 331 mmol · h/L | 640 mmol · h/L |

F. F. I. Rebecchi et al. investigated the prognostic value of the area under the H$^+$ curve (i.e., integrated acidity) in 36 healthy volunteers and 60 GERD patients. Based on a receiver operating characteristic analysis, the authors found that an area under the curve of hydrogen ion activity of above 100 mmol/L·min was very sensitive and specific (100% and 97%, respectively) for identifying patients with erosive esophagitis, and also had a good sensitivity and specificity (76% and 93%) for identifying patients with non-erosive GERD. See F. F. I. Rebecchi et al., "Improving the analysis of esophageal acid exposure by a new parameter: area under H$^+$", Am. J. Gastroenterol., Vol. 97, pp. 568-74 (2002); J. D. Gardner et al., "Determination of the reduction in gastric acidity necessary to prevent pathological oesophageal reflux in patients with gastro-oesophageal reflux disease treated with a proton pump inhibitor", Aliment Pharmacol. Ther., Vol. 17, pp. 955-64 (2003); J. D. Gardner at al., "Integrated acidity and rabeprazole pharmacology", Aliment Pharmacol Ther., Vol. 16, pp. 455-64 (2002); J. D. Gardner at al., "Integrated acidity and the pathophysiology of GERD", Am J Gastroenterol., Vol. 96, pp. 1363-70 (2001).

The pharmacodynamic parameter that best demonstrates the efficacy of an agent that works by inhibiting gastric acid is the "24 hour Integrated Gastric Acidity" ("IGA-24"). The most important measure of IGA is in the first 24 hours after the initial dose as PPI medicines have routinely not demonstrated a significant effect on inhibiting gastric acid secretion in the first 24 hours after an initial dose. Therefore, the IGA-24 on Day 1 ("IGA-24$_{Day\,1}$") is the most stringent measure of efficacy of PPI compositions. It is important to note that many studies performed on PPI drugs concomitantly administer pentagastrin to artificially stimulate the parietal cell in order to induce or artificially create efficacy on Day 1 of administration of the PPI. This creates an artificial effect on Day 1 and is not correlative to normal patients.

The pharmacokinetic parameter that predicts the efficacy of PPIs is area under the serum concentration vs. time curve, or area under the curve (AUC). See Cederberg et al., "Effect of omeprazole—a gastrin proton pump inhibitor—on pentagastrin stimulated acid secretion in man", Gut, Vol. 24, pp. 270-76 (1983); Cederberg et al., "Acid inhibitory characteristics of omeprazole in man", Scand. J. Gastroenterol. Suppl., Vol. 20, pp. 105-12 (1985); Cederberg et al., "Comparison of once-daily intravenous and oral omeprazole on pentagastrin-stimulated acid secretion in duodenal ulcer patients", Digestion, Vol. 53, pp. 171-78 (1985). Further, AUC above 1 micromolar of PPI (for substituted benzimidazoles) is an excellent predictor of efficacy. Further, the time that the AUC is above 1 micromolar of PPI (for substituted benzimidazoles) defines time that the PPI is significantly efficient at binding to the proton pumps in the parietal cell secretory canalicular membrane ("active proton pumps").

The pharmacokinetic equation for determining AUC is depicted below:

$$AUC = \frac{(f)\text{Dose} \times t_{1/2}}{0.693 \times V},$$

where f is bioavailability, $t_{1/2}$ is the half-life of the drug, and V is the volume of distribution of the drug. AUC is directly proportional to $t_{1/2}$, and as the $t_{1/2}$ increases, AUC gets larger. Since AUC is the major predictor of efficacy for PPI drugs, the prolongation of the half-life of the PPI (and as such increasing the AUC) directly results in the improvement of efficacy of PPIs.

Another more pharmacokinetic parameter that predicts efficacy is the AUC greater than concentration required to produce 50% inhibition (IC50), which is specific for each PPI.

Conversion rate of PPIs to the active moiety is also a determinant of efficacy, specifically as it relates to time and speed of onset after dosing. Therefore, it is desirable to combine two PPIs that have different half-lifes related to activation (activation half-lifes). For example, the activation half-life of lansoprazole and omeprazole complement one another with lansoprazole reaching 90% activity at an approximate pH of 1 to 1.5 in 7 to 8 minutes while omeprazole reaches 90% activity, at an approximate pH of 1 to 1.5, in 15 to 20 minutes. Unexpectedly, applicant found that when these two drugs are used together in the formulations herein described (as an example, 80 mg lansoprazole+80 mg omeprazole+1680 mg sodium bicarbonate) the half-life of both drugs in significantly prolonged. Normally the half-life of elimination of lansoprazole is 1 to 1.4 hrs (mean of approximately 1.2 hrs) and similarly for omeprazole, the elimination half-life is 0.7 to 1.2 hrs (mean of approximately 0.95 hr). When administered together, there is pharmacokinetic produce synergy. Omeprazole elimination half-life is prolonged to 1.9 hours (a prolongation factor of 200%) and the lansoprazole elimination half-life is prolonged to 3.7 hours (a prolongation factor of 300%).

Pharmacokinetic synergism refers to the enhancement in action or effect of a particular drug(s) compared to the individual effect of both the drugs combined. As provided in the Examples, combinations of omeprazole and lansoprazole significantly prolonged half-life of both drugs and improved $AUC_{0-24}$ and IGA-24 values, indicating enhanced efficacy of the PPIs. Individual values alone cannot account for this dramatic and unexpected increase in efficacy as demonstrated in the Examples. Rather, omeprazole and lansoprazole together affect and enhance the efficacy of the PPIs.

EXAMPLES

The examples below are for illustrative purposes only and are not to be construed as limiting the invention in any manner.

Example 1

The following table lists the daily dose half-life of various PPIs. Since half-life ($t_{1/2}$) and AUC have a high intersubject variability, it is important that $t_{1/2}$ be compared in the same subject in the same conditions with appropriate washout between studies.

TABLE 1

| PPI | Daily Dose | $t_{1/2}$ |
|---|---|---|
| Rabeprazole | 20-160 mg | 0.8-1 hr |
| Omeprazole | 20-160 mg | 0.9-1.5 hrs |
| Lansoprazole | 15-160 mg | 1-1.5 hrs |
| Tentaoprazole | 40-160 mg | 6.8-8 hrs |
| Pantoprazole | 40-160 mg | 1.2-1.5 hrs |
| Esomerprazole | 20-160 mg | 1.1-1.6 hrs |
| Dexlansoprazole | 15-160 mg | 1-1.6 hrs |

A list of drug combinations that produce prolonged half-lives, and found to be synergistic is shown in Table 2. Both PPIs can be delayed and/or immediate release. The doses of each PPI and cimetidine can range from 10 to 300 mg and 10 to 1500 mg, respectively.

TABLE 2

| PPI 1 | PPI 2 | Cimetidine |
|---|---|---|
| Ilaprazole | Omeprazole | No |
| Ilaprazole | Lansoprazole | No |
| Ilaprazole | Rabeprazole | No |
| Ilaprazole | Tenatoprazole | No |
| Ilaprazole | Pantoprazole | No |
| Ilaprazole | Esomeprazole | No |
| Ilaprazole | None | Yes |
| Ilaprazole | Omeprazole | Yes |
| Ilaprazole | Lansoprazole | Yes |
| Ilaprazole | Rabeprazole | Yes |
| Ilaprazole | Tenatoprazole | Yes |
| Ilaprazole | Pantoprazole | Yes |
| Ilaprazole | Esomeprazole | Yes |
| Lansoprazole | Omeprazole | No |
| Lansoprazole | Esomeprazole | No |
| Lansoprazole | Rabeprazole | No |
| Lansoprazole | Tenatoprazole | No |
| Lansoprazole | Pantoprazole | No |
| Lansoprazole | None | Yes |
| Lansoprazole | Omeprazole | Yes |
| Lansoprazole | Esomeprazole | Yes |
| Lansoprazole | Rabeprazole | Yes |
| Lansoprazole | Tenatoprazole | Yes |
| Lansoprazole | Pantoprazole | Yes |
| Rabeprazole | Omeprazole | No |
| Rabeprazole | Tenatoprazole | No |
| Rabeprazole | Pantoprazole | No |
| Rabeprazole | Esomeprazole | No |
| Rabeprazole | None | Yes |
| Rabeprazole | Omeprazole | Yes |
| Rabeprazole | Tenatoprazole | Yes |
| Rabeprazole | Pantoprazole | Yes |
| Rabeprazole | Esomeprazole | Yes |
| Omeprazole | Tenatoprazole | No |
| Omeprazole | Pantoprazole | No |
| Omeprazole | Esomeprazole | No |
| Omeprazole | Tenatoprazole | Yes |
| Omeprazole | Pantoprazole | Yes |
| Omeprazole | Esomeprazole | Yes |
| Pantoprazole | Tenatoprazole | No |
| Pantoprazole | Esomeprazole | No |
| Pantoprazole | Tenatoprazole | Yes |
| Pantoprazole | Esomeprazole | Yes |
| Tenatoprazole | Esomeprazole | No |
| Tenatoprazole | Esomeprazole | Yes |
| Ilaprazole | None | Yes |
| Lansoprazole | None | Yes |
| Rabeprazole | None | Yes |
| Pantoprazole | None | Yes |
| Tenatoprazole | None | Yes |
| Esomeprazole | None | Yes |

The PPIs are listed as the racemate and as the base form. However, this list is meant to include the enantiomers, based upon the USAN Handbook, and the salt forms with hydrate (examples include, but are not limited to, pantoprazole sodium, tenatoprazole sodium trihydrate, and esomeprazole magnesium). The USAN Handbook, Chicago, Ill.: US Adopted Names Program (1999).

In one embodiment disclosed herein provide for a solid dosage form comprising all or any: omeprazole (60 mg)+lansoprazole (60 mg)+cimetidine HCl (200 mg)+sodium bicarbonate (1680 mg)+croscarmellose sodium (25 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

In another embodiment disclosed herein provide for a solid dosage form comprising all or any: omeprazole (60 mg)+lansoprazole (60 mg)+sodium bicarbonate (1200 mg)+calcium carbonate (400 mg)+croscarmellose sodium (25 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

Another embodiment disclosed herein provide for a solid dosage form comprising all or any: omeprazole (60 mg)+lansoprazole (60 mg)+sodium bicarbonate (1200 mg)+magnesium hydroxide (420 mg)+sodium carboxymethylcellulose (30 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

Another embodiment disclosed herein provide for a solid dosage form comprising all or any: omeprazole (60 mg)+lansoprazole (60 mg)+sodium bicarbonate (1200 mg)+calcium carbonate (300 mg)+calcium formate (100 mg)+croscarmellose sodium (25 mg)+pregelatinized starch (65 mg)+magnesium stearate (25 mg). Further, aspirin (80 to 325 mg) or NSAIDs in their normal dosages, such as naproxen (100 to 500 m2) can be added to the embodiments.

Another embodiment disclosed herein provide for a solid dosage form comprising all or any: omeprazole (60 mg)+lansoprazole (60 mg)+sodium bicarbonate (1200 mg)+calcium carbonate (300 mg)+calcium formate (100 mg)+sodium carboxymethylcellulose (30 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

Another embodiment disclosed herein provide for a solid dosage form comprising all or any: omeprazole (70 mg)+lansoprazole (30 mg)+sodium bicarbonate (1200 mg)+calcium carbonate (300 mg)+calcium formate (100 mg)+croscarmellose sodium (25 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

Another embodiment disclosed herein provide for a solid dosage form comprising all or any: omeprazole (70 mg)+lansoprazole (30 mg)+sodium bicarbonate (1200 mg)+calcium carbonate (300 mg)+calcium formate (100 mg)+sodium carboxymethylcellulose (30 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

Another embodiment disclosed herein provide for a solid dosage form comprising all or any: omeprazole (60 mg)+lansoprazole (60 mg)+sodium bicarbonate (1000 mg)+calcium carbonate (400 mg)+calcium formate (200 mg)+magnesium hydroxide (200 mg)+croscarmellose sodium (25 mg)+pregelatinized starch (65 mg)+magnesium stearate (25 mg). Further, aspirin (80 to 325 mg) or NSAIDs in their normal dosages, such as naproxen (100 to 500 mg) can be added to the embodiments.

Still another embodiment disclosed herein provide for a solid dosage form comprising all or any: omeprazole (60 mg)+lansoprazole (60 mg)+cimetidine HCl (400 mg)+calcium carbonate (1200 mg)+magnesium hydroxide (200 mg)+croscarmellose sodium (25 mg)+pregelatinized starch (65 mg)+magnesium stearate (25 mg). Further, aspirin (80 to 325 mg) or NSAIDs in their normal dosages, such as naproxen (100 to 500 mg) can be added to each of the aforementioned embodiments.

A skilled artisan would appreciate that the foregoing embodiments in paragraphs [00181]-[00189] would also contemplate the following ratios of omeprazole to lansoprazole: about 40:40, about 50:50, about 75:75 and about 80:80.

Example 2

A study was performed as a cross-over design, with washout between doses. The subject received the test article after placing a Bravo pH probe in the stomach and verifying its placement with pH readings of less than 2. After a baseline evaluation, to ensure that the pH probe is in the correct place for reading gastric acid in the stomach, the subject has an intravenous access established and a baseline blood draw was taken to provide evidence of a lack of PPI in the blood at baseline. The subject received the one of three different formulations, and the time of administration was noted. Blood draws were taken at intervals to characterize the absorption, distribution and elimination phases of the test article. From these data the AUC was calculated. Continuous gastric pH recording was made utilizing the Bravo pH probe and radiofrequency receiver. Gastric pH values were recorded every 10 seconds. From these data the IGA was determined for the 24 hour period.

The results for three different formulations are summarized below:

|  | Formulation 1<br>80 mg Omeprazole +<br>80 mg Lansoprazole +<br>1680 mg NaHCO$_3$ | [Formulation 2]<br>160 mg Omeprazole +<br>1680 mg NaHCO$_3$ | [Formulation 3]<br>160 mg Lansoprazole +<br>1680 mg NaHCO$_3$ |
|---|---|---|---|
| $AUC_{0-24}$ | 23.7 µg · hr/mL | 18.1 µg · hr/mL | 12.4 µg · hr/mL |
| $AUC > 1 \mu M_{0-24}$ | 18.9 µg · hr/mL | 13.6 µg · hr/mL | 9.3 µg · hr/mL |
| $IGA\text{-}24_{Day\ 1}$ | 38 mmol · h/L | 178 mmol · h/L | 57 mmol · h/L |

Example 3

A study was performed as a cross-over design, with washout between doses. The subject received the test article after placing a Bravo pH probe in the stomach and verifying its placement with pH readings of less than 2. After a baseline evaluation, to ensure that the pH probe is in the correct place for reading gastric acid in the stomach, the subject has an intravenous access established and a baseline blood draw was taken to provide evidence of a lack of PPI in the blood at baseline. The subject received the one of three different formulations, and the time of administration was noted. Blood draws were taken at intervals to characterize the absorption, distribution and elimination phases of the test article. From these data the AUC was calculated. Continuous gastric pH recording was made utilizing the Bravo pH probe and radiofrequency receiver. Gastric pH values were recorded every 10 seconds. From these data the IGA was determined for the 24 hour period.

The results for three different formulations are summarized below:

|  | Formulation 4<br>50 mg Omeprazole +<br>50 mg Lansoprazole +<br>1680 mg NaHCO$_3$ | Formulation 5<br>100 mg Omeprazole +<br>1680 mg NaHCO$_3$ | Formulation 6<br>100 mg Lansoprazole +<br>1680 mg NaHCO$_3$ |
|---|---|---|---|
| AUC$_{0-24}$ | 5.9 µg · hr/mL | 4.2 µg · hr/mL | 2.9 µg · hr/mL |
| AUC > 1 µM$_{0-24}$ | 3.1 µg · hr/mL | 2.2 µg · hr/mL | 1.8 µg · hr/mL |
| IGA-24$_{Day\ 1}$ | 190 mmol · h/L | 274 mmol · h/L | 241 mmol · h/L |

Example 4

A study was performed as a cross-over design, with washout between doses. The subject received the test article after placing a Bravo pH probe in the stomach and verifying its placement with pH readings of less than 2. After a baseline evaluation, to ensure that the pH probe is in the correct place for reading gastric acid in the stomach, the subject has an intravenous access established and a baseline blood draw was taken to provide evidence of a lack of PPI in the blood at baseline. The subject received the one of eighteen different formulations, and the time of administration was noted. Blood draws were taken at intervals to characterize the absorption, distribution and elimination phases of the test article. From these data the AUC was calculated. Continuous gastric pH recording was made utilizing the Bravo pH probe and radiofrequency receiver. Gastric pH values were recorded every 10 seconds. From these data the IGA was determined for the 24 hour period.

IR: Immediate-release means that this portion of the composition is formulated so that delivery begins in the stomach and there is no enteric coating or timed release coating involved. The term is intended to refer to any PPI formulation in which all or part of the PPI is in solution either before administration or immediately (i.e., within about 30 minutes) after administration. For example, with an "immediate release" formulation, oral administration results in immediate release of the agent from the composition into gastric fluid.

DR: Delayed release means that release of this component of the formulation begins at a time other than promptly after administration. Delayed release formulations includes any nonimmediate release formulation, including but not limited to, film-coated formulations, enteric-coated formulations, encapsulated formulations, sustained release formulations and pulsatile release formulations. For delayed release formulations, the rate of release of drug from the dosage form is the rate-limiting step in the delivery of the drug to the target area.

The results of the different formulations are summarized below:

|  | Formulation 7<br>120 mg Omeprazole +<br>200 mg Cimetidine +<br>1680 mg NaHCO$_3$ | Formulation 8<br>40 mg Omeprazole +<br>1680 mg NaHCO$_3$ | Formulation 9<br>120 mg Rabeprazole +<br>200 mg Cimetidine +<br>1680 mg NaHCO$_3$ |
|---|---|---|---|
| AUC$_{0-24}$ | 12.9 µg · hr/mL<br>Omeprazole | 2.6 µg · hr/mL<br>Omeprazole | 7.1 µg · hr/mL<br>Rabeprazole |
| Half-life (t$_{1/2}$) | 2.1 hrs<br>Omeprazole | 1.1 hrs<br>Omeprazole | 0.8 hrs<br>Rabeprazole |
| IGA-24$_{Day\ 1}$ | 56 mmol · hr/L | 202 mmol · hr/L | 173 mmol · hr/L |

|  | Formulation 10<br>80 mg Omeprazole IR +<br>80 mg Lansoprazole DR +<br>1680 mg NaHCO$_3$ | Formulation 11<br>40 mg Esomeprazole DR | [Formulation 12]<br>120 mg Omeprazole IR +<br>40 mg Tenatoprazole IR +<br>200 mg Cimetidine +<br>1680 mg NaHCO$_3$ |
|---|---|---|---|
| AUC$_{0-24}$ | 7.6 µg · hr/mL<br>Omeprazole<br>14.7 µg · hr/mL<br>Lansoprazole | 3.6 µg · hr/mL<br>Esomeprazole<br>— | 11.8 µg · hr/mL<br>Omeprazole<br>88.3 µg · hr/mL<br>Tenatoprazole |
| AUC$_{0-24\ Combined}$ | 22.3 µg · hr/mL<br>Lansoprazole | — | — |
| Half-life (t$_{1/2}$) | 1.6 hrs<br>Omeprazole<br>2.5 hrs<br>Lansoprazole | 1.4 hrs<br>Esomeprazole<br>— | 1.8 hrs<br>Omeprazole<br>12.9 hrs<br>Tenatoprazole |
| IGA-24$_{Day\ 1}$ | 115 mmol · hr/L | 316 mmol · hr/L | 28.4 mmol · hr/L |

|  | Formulation 13<br>120 mg Tentaprazole IR +<br>1680 mg NaHCO$_3$ | Formulation 14<br>100 mg Pantoprazole IR +<br>60 mg Omeprazole IR +<br>1680 mg NaHCO$_3$ | Formulation 15<br>160 mg Omeprazole IR +<br>1680 mg NaHCO$_3$ |
|---|---|---|---|
| AUC$_{0-24}$ | 76.9 µg · hr/mL<br>Tentaprazole<br>— | 22.6 µg · hr/mL<br>Pantoprazole<br>2.4 µg · hr/mL<br>Omeprazole | 18.1 µg · hr/mL<br>Omeprazole<br>— |

| | | | |
|---|---|---|---|
| Half-life ($t_{1/2}$) | 8.6 hrs Tentaprazole — | 1.5 hrs Pantoprazole 0.8 hrs Omeprazole | 2.3 hrs Omeprazole — |
| IGA-24$_{Day\,1}$ | >400 mmol · hr/L | >400 mmol · hr/L | 178 mmol · hr/L |

| | [Formulation 16] 160 mg Lansoprazole IR + 1680 mg NaHCO$_3$ | Formulation 17 40 mg Omeprazole IR + 40 mg Tenatoprazole IR + 1680 mg NaHCO$_3$ | Formulation 18 60 mg Lansoprazole IR + 40 mg Tenatoprazole ER + 1680 mg NaHCO$_3$ |
|---|---|---|---|
| AUC$_{0-24}$ | 12.4 µg · hr/mL Lansoprazole — | 2.3 µg · hr/mL Omeprazole 56.3 µg · hr/mL Tenatoprazole | 2.9 µg · hr/mL Lansoprazole 48.4 µg · hr/mL Tenatoprazole |
| Half-life ($t_{1/2}$) | 2.4 hrs Lansoprazole — | 0.9 hrs Omeprazole 10.6 hrs Tenatoprazole | 1.6 hrs Lansoprazole 7.9 hrs Tenatoprazole |
| IGA-24$_{Day\,1}$ | 57 mmol · hr/L | >400 mmol · hr/L | >400 mmol · hr/L |

| | Formulation 19 40 mg Esomeprazole DR + 60 mg Lansoprazole IR + 1680 mg NaHCO$_3$ | Formulation 20 60 mg Omeprazole IR + 60 mg Pantoprazole IR + 1680 mg NaHCO$_3$ | Formulation 21 120 mg Lansoprazole IR + 1680 mg NaHCO$_3$ |
|---|---|---|---|
| AUC$_{0-24}$ | 2.7 µg · hr/mL Esomeprazole 4.0 µg · hr/mL Lansoprazole | 3.8 µg · hr/mL Omeprazole 8.9 µg · hr/mL Pantoprazole | 2.7 µg · hr/mL Lansoprazole — |
| Half-life ($t_{1/2}$) | 1.1 hrs Esomeprazole 2.6 hrs Lansoprazole | 1.7 hrs Omeprazole 1.1 hrs Pantoprazole | 2.4 hrs Lansoprazole — |
| IGA-24$_{Day\,1}$ | >400 mmol · hr/L | 109 mmol · hr/L | >400 mmol · hr/L |

| | Formulation 22 120 mg Pantoprazole IR + 1680 mg NaHCO$_3$ | Formulation 23 120 mg Omeprazole IR + 1680 mg NaHCO$_3$ |
|---|---|---|
| AUC$_{0-24}$ | 9.2 µg · hr/mL Pantoprazole | 9.6 µg · hr/mL Omeprazole |
| Half-life ($t_{1/2}$) | 0.9 hrs Pantoprazole | 1.9 hrs Omeprazole |
| IGA-24$_{Day\,1}$ | >400 mmol · hr/L | >400 mmol · hr/L |

Example 5

Overview: A prospective, randomized study can be conducted to evaluate the regression of Barrett's esophagus, in patients diagnosed with Barrett's esophagus, following treatment with Nexium® (esomeprazole) as compared to test article. Patients with Barrett's esophagus, with or without low grade dysplasia, can be randomized to receive Nexium® 40 mg once daily or the test article once daily.

Introduction. Barrett's esophagus is related to acid reflux into the esophagus. In general, it is thought that chronic acid reflux leads to Barrett's which leads to low and then high grade dysplasia which leads to adenocarcinoma of the esophagus. J W van Sandick, "Impact of endoscopic biopsy surveillance of Barrett's oesophagus on pathological stage and clinical outcome of Barrett's carcinoma", GUT, Vol. 43, pp. 216-222 (1998). The incidence of all of these conditions is increasing in the U.S. Adenocarcinoma of the esophagus is the most rapidly growing cancer. Patients with Barrett's esophagus are currently managed by repeat endoscopic surveillance with biopsy/pathological evaluation. If changes in pathology of biopsied areas are noted to involve low or high grade dysplasia, patients are monitored more frequently (low grade dysplasia) or evaluated for other procedures such as ablation, mucosal resection or esophagectomy (high grade dysplasia). If carcinoma is noted, then esophagectomy is often recommended. Currently, there is no medical treatment to reverse Barrett's esophagus to normal squamous esophageal mucosa. In a review of prospective studies of the treatment of BE with proton pump inhibitors (PPIs) (with or without surgery), only 3 of 123 patients had complete apparent reversal of BE. Sampliner, R., "Reduction of Acid Exposure and Regression of Barrett's Esophagus", Digestive Diseases, Vol. 18(4), pp. 203-207 (2001).

Nighttime acid break-through (pH below 4 for more than 60 consecutive minutes in patients on twice daily PPI therapy) occurs in over 70% of patients. Thompson, C A., "First federal comparative effectiveness review examines GI disorder", Am J Health-Syst Pharm, Vol. 63, pg. 302 (2006). The addition of an H2 blocker at bedtime has been suggested as a method to control nocturnal acid breakthrough, however, this has been shown to be effective for only one week, then tolerance develops and the nighttime effects of the H2 blocker are eliminated. Janiak P, 'Clinical trial: the effects of adding ranitidine at night to twice daily omeprazole therapy on nocturnal acid breakthrough and acid reflux in patients with systemic sclerosis—a randomized controlled, cross-over trial", Alimentary Pharmacology Therapeutics, Vol. 26, pp. 1259-1265 (2007). Esomeprazole (Nexium®) 40 mg is a potent inhibitor of proton pumps and is widely used for acid-related disorders. The test article can be a PPI combination developed at the University of Missouri to maximize the AUC (area under the serum concentration vs time curve) of PPI and is capable of producing and maintaining pH values at >4 for 24 hours per day after Day 1 of treatment.

Methods

Null Hypothesis: There will be no difference in the rate of reversal of patients with Barrett's whether they receive Nexium® 40 mg once daily or test article once daily.

Alternative Hypothesis: There will be a difference in the rate of reversal of patients with Barrett's whether they receive Nexium® 40 mg once daily or test article once daily.

Sample size. Data from the literature suggest a 2.4% incidence of complete reversal of Barrett's after 24 months of treatment with PPI. Based upon the achievement of complete control of pH with pH values maintained above 4 for 24 hours per day, a reversal rate of 50% can be expected in the test article arm. Based upon these assumptions, a sample size of 10 subjects per arm will be needed to detect a difference if one assumes a Type I error rate of 5% and a Type II error rate of 20%.

Patients can be evaluated every 3 months by endoscopy-guided biopsy. Pathology results will be compared at 3 months 6 months and 9 months for signs of reversal of Barrett's or reversal of dysplastic lesions. Partial reversal and complete reversal can be compared. Biopsy protocols using acetic acid test for standard, non-magnifying endoscopic detection of biopsy areas and jumbo forceps/4-quadrant biopsies every 1 cm can be employed. Vazquez-Iglesias, J L., "Acetic acid allows effective selection of areas for obtaining biopsy samples in Barrett's esophagus", European Journal of Gastroenterology & Hepatology. Vol. 19(3), pp. 187-193 (2007).

Test article can comprise: omeprazole powder (80 mg)+lansoprazole powder (80 mg)+sodium bicarbonate (1680 mg)+croscarmellose sodium (25 mg)+pregelatinized starch (65 mg)+magnesium stearate (25 mg).

Example 6

Overview: A double-blind, randomized study may be performed to compare 80 mg omeprazole plus 80 mg lansoprazole with Zegrid® 40 mg in normal, healthy adults. The study can include a cross-over design with washout between doses. Participants need to fast starting midnight of the day of visit (Day 1). The participant can receive a Bravo pH probe into their stomach and verifying its placement with pH readings of less than 2. The participant can also have an intravenous access established. Prior to PPI administration, participant can be given breakfast, after which a 5 mL pre-dose blood sample can be collected. After the dose of one of the study drugs, 4 mL blood collections can be taken at 5, 15, 60, 45, 60, 75, 135, 195, 315, and 375 minutes. At the noon hour, the participant can be given lunch. The IV can be removed after the 375 minute blood draw, but the participant can keep the Bravo pH probe in their stomach for a total of 24 hours. Participant can be allowed to eat after the 375 minute blood draw. There can be a 7-day washout period. Afterwards (Day 8), the other study drug can be tested following the same protocol as described above.

The study can measure the level of IGA, the pharmacokinetics of the drug, such as elimination half-life ($t_{1/2}$), AUC and maximum concentration ($C_{max}$), and the level of Grastrin-17 in the participant's bloodstream. Each of the parameters can aid in the determination of the efficacy of the study drugs. Gastrin concentrations directly relate to the activity of the parietal cells, which are responsible for acid production in the stomach. The PPI inhibits the proton pump and prevents the production of acid. Therefore, the gastrin results, in conjunction with the pH, can help determine the effectiveness of the PPI at suppressing acid production.

Protocol

Schedule of Events

This study will have two treatment periods, one for each study medication treatment arm. The participant will be randomized to one treatment arm. After completion and washout, they will be placed on the other treatment arm.

Study Day Minus: Participant will sign the informed consent and HIPAA forms. All study procedures will be explained and all questions will be answered. The participant will be informed they need to be fasting starting at midnight on Study Day 1. At this visit, their concomitant medications will be recorded, as well as relevant medical/surgical history. The inclusion/exclusion criteria will be evaluated. If the participant needs to complete a washout period, their Study Day 1 will be scheduled to provide the needed washout time. Study Day 1 will also be scheduled according to their personal schedule and such that all visit days will fall on Monday through Friday.

Study Day 1: Participant will need to be fasting starting midnight the day of the visit. Concomitant medications will be reviewed and they must meet all inclusion and no exclusion criteria. They will be provided a breakfast and a lunch meal and allowed to drink only water before and during the visit. For females of child-bearing potential, a urine sample will be collected for a urine pregnancy test. A 20 gauge IV catheter will be inserted into their hand or arm for approximately eleven 4 mL blood collections. The participant will swallow, with water, a tethered swallowable Bravo pH probe into their stomach under appropriate supervision. The string will have a bead attached, at the participant's lip, to mark placement of the string in order to keep the probe suspended in the stomach. The string will be secured to the participant's cheek and neck with two tegaderms. After successfully swallowing the Bravo pH probe, and before medication is taken, the participant will be given a McDonald's Egg McMuffin to eat for breakfast. While data from the probe is being collected they will keep the pH probe receiver within five feet of themselves at all times. A 5 mL pre-dose blood sample will be collected. The participant will take the dose of study drug. There will be 4 mL blood collections at 5, 15, 30, 45, 60, 75, 135, 195, 315, and 375 minutes after the dose. At the noon hour, the participant will be given a McDonald's cheeseburger and medium french fries for the noon meal. The IV will be removed after the 375 minute blood draw and the participant will keep the Bravo pH probe in their stomach for a total of 24 hours. They will be allowed to eat again after the 375 minute blood draw.

Study Day 2: The participant will return for collection of the pH probe receiver and recorded data. The participant will have two options for removal of the probe. The string may be cut below the point the bead is attached so the probe and string will pass through the digestive system. The probe may also be withdrawn from the stomach by appropriate staff. If resistance is met, the string will be cut below the bead and appropriate personnel will be notified.

Study Day 8: The participant will enter the second treatment period and will take the second arm of study medication. Participant will need to be fasting starting midnight the day of the visit. They will be provided a breakfast and a lunch meal and allowed to drink only water before and during the visit. For females of child-bearing potential, a urine sample will be collected for a urine pregnancy test. A 20 gauge IV catheter will be inserted into their hand or arm for approximately eleven 4 mL blood collections. The participant will swallow, with water, a tethered swallowable Bravo pH probe into their stomach under the appropriate supervision. The string will have a bead attached, at the patient's lip, to mark placement of the string to keep the probe suspended in the stomach. The string will be secured to the participant's cheek and neck with two tegaderms. After successfully swallowing the Bravo pH probe, and before medication is taken, the participant will be given a McDonald's Egg McMuffin to eat for breakfast. While data from the probe is being collected they will keep the pH probe receiver within five feet of themselves at all times. A 5 mL pre-dose blood sample will be collected. The participant will take the dose of study drug and blood will be collected at 5, 15, 30, 45, 60, 75, 135, 195, 315, and 375 minutes after the dose. At the noon hour, the participant will be given a McDonald's cheeseburger and medium french fries for the noon meal. The IV will be removed after the 375 minute blood draw and the participant will keep the Bravo pH probe in their stomach for a total of 24 hours. They will be allowed to eat again after the 375 minute blood draw.

Study Day 9: The participant will return for collection of the pH probe receiver and recorded data. The participant will have two options for removal of the probe. The string may be cut below the point the bead is attached so the probe and string will pass through the digestive system. The probe may also be withdrawn from the stomach by appropriate personnel. If resistance is met, the string will be cut below the bead and appropriate personnel will be notified. The participant will receive a compensation check.

Abbreviations
AE=Adverse Event
AUC=Area Under the Curve
b.i.d.=Twice daily
CRF=Case Report Form
FDA=Food and Drug Administration
GERD=Gastroesophageal Reflux Disease
IDS=Investigational Drug Services
IRB=Institutional Review Board
mg=milligrams
mL=milliliters
NSAID=Non-Steroidal Anti-Inflammatory Drug
PPI=Proton Pump Inhibitor
SAE=Serious Adverse Event
t.i.d.=Three Times per Day
UMHC=University of Missouri Health Care
ZES=Zollinger-Ellison syndrome Background Information Omeprazole (the active ingredient in Zegerid and Prilosec) and Lansoprazole (the active ingredient in Prevacid) are two FDA-approved drugs that are commonly used to treat a wide variety of gastric acid-related disorders, including gastric and duodenal ulcers, gastroesophageal reflux disease (GERD), and Zollinger-Ellison Syndrome (ZES). They belong to a class of antisecretory compounds called the substituted benzimidazoles and act by inhibiting the proton pumps in the parietal cells (hence the term "Proton Pump Inhibitor," abbreviated as "PPI"), thereby blocking the final step of gastric acid production. In clinical studies, the mean plasma elimination half-life in healthy adults has been found to be about 1.5 hours for lansoprazole[1] and less than 1 hour for omeprazole[2]. The acid inhibitory effect—which was measured by the decrease in basal acid output, increase in mean gastric pH, and percent time the gastric pH was greater than 3 and 4—lasted more than 24 hours on the fifth day of treatment with a 30 mg dose of lansoprazole or with a 40 mg dose of omeprazole according to the package inserts for Prevacid and Prilosec, respectively. The drugs also significantly reduced meal-stimulated gastric acid output and secretion volume as well as pentagastrin-stimulated acid output on the fifth day. On the first few days of treatment, however, efficacy is usually low and acid inhibition rarely lasts for longer than 2-3 hours[3,4].

Lansoprazole has been shown in many studies to be extensively metabolized in the liver in approximately equal amounts by both the 2C19 and 3A4 isoforms of the Cytochrome P450 enzyme[5], while omeprazole is metabolized mostly by the 2C19 isoform[6]. Following a single oral dose, most of the PPI detected in the urine is in the inactive metabolized form[7]. Elimination rates have been found to be faster in pediatric patients and slower in geriatric patients and dosing adjustments for these populations have been suggested in various past studies[8]. No differences in PPI pharmacokinetics and intragastric pH between males and females have been reported[3,4]. Patients with renal insufficiency had a shortened elimination half-life and a decreased total AUC[9,10], while patients with hepatic diseases had significantly extended elimination half-lives and increased total AUC[10,11]. Over 10,000 patients have been treated with both PPIs in Phase 2 and 3 clinical trials and each drug is regularly used in clinical settings to control various acid-related disorders.

Because of the high specificity of PPIs, side effects are usually rare and mild. Omeprazole and lansoprazole are both pro-drugs that are only converted to their active form at pH of below 2 and since the only physiological location that satisfies this requirement is the parietal cell canalicular space; the effects of the drugs are limited only to this area. Adverse effects as reported by the package inserts for each drug are outlined below:

TABLE 1

Adverse effects (in terms of % of patients) that were found in at least 1% of patients taking either drug in clinical trials[3,4].

| | Zegerid ™ package insert | | Prevacid ® package insert | |
|---|---|---|---|---|
| Effect | Omeprazole (n = 2631) | Placebo (n = 120) | Lansoprazole (n = 2768) | Placebo (n = 1023) |
| Abdominal pain | 5.2 | 3.3 | 2.1 | 1.2 |
| Asthenia | 1.3 | 0.8 | <1 | N/R |
| Constipation | 1.5 | 0.8 | 1.0 | 0.4 |
| Diarrhea | 3.7 | 2.5 | 3.8 | 2.3 |
| Headache | 2.9 | 2.5 | <1 | <1 |

Oral administration of PPI drugs is typical. The hypothesis that will be tested in this study is that there is no difference in 24-hour integrated gastric acidity between subjects receiving a single 40 mg dose of Zegerid and subjects receiving a single dose of 80 mg omeprazole plus 80 mg lansoprazole in an immediate-release formulation; the alternate hypothesis is that there is a difference in 24-hour integrated gastric acidity subjects receiving a single 40 mg dose of Zegerid and subjects receiving a single dose of 80 mg omeprazole plus 80 mg lansoprazole in an immediate-release formulation. Therefore, by design, a single dose will be given.

Population to be Studied

Normal, healthy adults between the ages of 18 and 60 that volunteer for participation.

References

References to literature and data that are relevant to the trial and that provide background for the trial:
1. Karol, M. D., Pharmacokinetics of lansoprazole in hemodialysis patients.
2. Cederberg, C., Omeprazole: pharmacokinetics and metabolism in man.
3. Prilosec delayed-release capsules. In AstraZeneca: Wilmington, Del., 2002.

4. Prevacid delayed-release capsules. In TAP Pharmaceuticals: Lake Forest, Ill., 2003.
5. Pichard, L.; Curi-Pedrosa, R.; Bonfils, C.; Jacqz-Aigrain, E.; Domergue, J.; Joyeux, H., Oxidative metabolism of lansoprazole by human liver cytochromes P450. *Molecular Pharmacology* 1995, 47, (2), 410-8.
6. Yamazaki, H.; Inoue, K.; Shaw, P. M.; Checovich, W. J.; Guengerich, F. P.; Shimada, T., Different contributions of cytochrome P450 2C19 and 3A4 in the oxidation of omeprazole by human liver microsomes: effects of contents of these two forms in individual human samples. *Journal of Pharmacology and Experimental Therapeutics* 1997, 283, (2), 434-42.
7. Sohn, D. R.; Kobayashi, K.; Chiba, K.; Lee, K. H.; Shin, S. G.; Ishizaki, T., Disposition kinetics and metabolism of omeprazole in extensive and poor metabolizers of S-mephenyloin 4'-hydroxylation recruited from an Oriental population. *Journal of Pharmacology and Experimental Therapeutics* 1992, 262, (3), 1195-202.
8. Phillips J O, B. J., Siddiqi S H, Bothwell M, Pediatric patients have shorter lansoprazole half-life than previously reported. *American Journal of Gastroenterology* 2007, 102, (s2), S548.
9. Naesdal, J.; Andersson, T.; Bodemar, G.; Larsson, R.; Regårdh, C. G.; Skånberg, I., Pharmacokinetics of [14C] omeprazole in patients with impaired renal function. *Clinical Pharmacology & Therapeutics* 1986, 40, (3), 344-51.
10. Delhotal-Landes, B.; Flouvat, B.; Duchier, J.; Molinie, P.; Dellatolas, F.; Lemaire, M., Pharmacokinetics of lansoprazole in patients with renal or liver disease of varying severity. *European Journal of Clinical Pharmacology* 1993, 45, (4), 367-71.
11. Yin, O. Q. P.; Brian, T.; Albert, H. L. C.; Mary, M. Y. W.; Moses, S. S. C., Omeprazole as a CYP2C19 marker in Chinese subjects: assessment of its gene-dose effect and intrasubject variability. *The Journal of Clinical Pharmacology* 2004, 44, (6), 582-9.

Trial Objectives and Purpose

Hypothesis. The hypothesis that will be tested in this study is; that there is no difference in 24-hour integrated gastric acidity between subjects receiving a single 40 mg dose of Zegerid and subjects receiving a single dose of 80 mg omeprazole plus 80 mg lansoprazole in an immediate-release formulation; the alternate hypothesis will be that there is a difference in 24-hour integrated gastric acidity subjects receiving a single 40 mg dose of Zegerid and subjects receiving a single dose of 80 mg omeprazole plus 80 mg lansoprazole in an immediate-release formulation.

Trial Design

Primary endpoint. The primary endpoint will be the integrated gastric acidity over 24 hours. pH probe data will be transformed into integrated gastric acidity using the AcidipHy software.

This trial is a double-blind, single site trial.

Measures taken to avoid/minimize bias. The study medication will be double-blind. A single dose of one of the study medication arms will be given for each treatment period for a total of two doses of study medication.

Length of participation. The participant will participate in the trial for a minimum of 10 days. Required washout before Study Day 1 will cause the length of participation to vary slightly among participants. The Study Day Minus visit will last about half an hour. The Day 1 visit will last approximately 24 hours because the participant will keep the probe in their stomach for 24 hours. The Day 2 visit will last 30 minutes. There will then be a 7-day washout period between study drugs. The Day 8 visit will last approximately 24 hours because the participant will keep the probe in their stomach for 24 hours, and the Day 9 and final visit will last 30 minutes.

Storage of investigational products. The investigational products will be dispensed only by the pharmacist in charge of investigational drug trials. Bravo pH probes, tethering equipment and blood draw supplies will be stored at the study site.

Dispensing investigational products. The investigational products will be dispensed in a 50 mL centrifuge tube. Before the study drug is consumed by the participant, 30 mL of water will be added and mixed.

Randomization codes. Maintenance of trial treatment randomization codes and procedures for breaking codes is as follows: the blind may be broken in the case of a serious adverse event. The IDS pharmacist in charge of the study drug and in charge of randomizing the participant will have a participant list and information on what study medication they are taking. The participant will be given a card to carry with them stating that they are enrolled in a clinical trial, brief details of the trial and who to call in case of an emergency.

Data to be recorded on the CRF. Participant initials, sex, date of birth, ethnicity, pregnancy and lactation status, inclusion/exclusion criteria, concomitant medications, relevant medical history, blood test data, pH probe data, time of blood collections and the time of consumption of the study medication, any use of a prohibited medication and adverse events.

Methods

Study drug form. The study drugs will be in the form of a suspension consisting of powder for oral administration mixed with 30 mL of water.

Methods used to identify and recruit participants. Word of mouth.

Methods used to avoid inadvertent coercion in the recruitment process. Potential participants will receive written informed consent information. The participants will be assured that they have the right to not participate.

Bravo pH probe. The Bravo pH probe will be deployed from its delivery system so that the probe is separate from the delivery mechanism before it is swallowed by the patient. A 0.1 mm diameter polyester braided tethering string will be tied securely around the pin at the top of the probe in order to secure the string to the probe. A bead will be attached to the string at the patient's lip to mark placement. Two tegaderms will be used to secure the string to the participant's cheek.

Pregnancy and lactation screening. Female participants of child-bearing potential will be administered a urine pregnancy test. They will be verbally asked if they are lactating.

Consent and Assent Processes and Documents

Type of Consent Process: Written

Description of the consent process. The study will be explained in full detail. The participant will be allowed time to read the consent. All questions will be answered. After verbal assent is made, the participant will sign the consent. The original will be kept with the study documents and the subject will be given a copy.

Voluntary participation. A participant may decide to participate in this study or not to participate. If the participant chooses not to participate, he or she may leave the study at any time. The participant's decision will not affect the care the participant will receive from any medical care provider or medical benefits to which the participant is entitled. If the participant decides to withdraw from the study at a later date, we will keep the information we have collected up to that point but will not ask the participant for any more information. We will continue to use the data and specimens the participant provided up to that time unless we get a signed written request from the participant asking us not to do so.

The investigator(s) conducting the study may also decide to withdraw the participant from the study without his or her consent if it is determined that the participant is not actually eligible or is no longer able to complete the requirements of the study.

Blood Collection

All IV insertions will be performed by a registered nurse or by a licensed practical nurse who is certified to start IVs. The goal of the blood collection is to characterize the pharmacokinetics of omeprazole and lansoprazole in the subjects and to determine the levels of Gastrin-17 over the course of the collection period. An occasional blood sample may be collected slightly outside of the scheduled time. The characterization of pharmacokinetics can accommodate different times if the actual time of blood collection is recorded. The scheduled and actual time of the blood collection will be recorded on the CRF. If the IV becomes occluded and another cannot be started in time for the next scheduled blood draw, a butterfly needle will be used to obtain the needed blood sample. Every effort will be made to adhere to the blood draw schedule. Over the course of two treatment periods twenty 4-mL blood samples and two 5 mL blood samples will be collected, for a total of 90 mL of blood. After each blood collection approximately 3-5 mL of 0.9% Sodium Chloride will be flushed through the participant's IV catheter to prevent blockage in the IV cannula.

Banking. Blood will not be banked (kept indefinitely), for use in other research not related to this project.

Selection and Withdrawal of Subjects

Inclusion Criteria

1. Adult between 18 and 60 years of age.
2. If a female is of child-bearing potential, they must be using an acceptable form of birth control: oral contraceptive, intra-uterine device, contraceptive patch, injection, or vaginal ring, double-barrier method i.e. condoms and spermicide, tubal ligation, abstinence, or male partner with a vasectomy.
3. Ability to swallow a multi-vitamin sized pill with water, without difficulty.
4. Willing and able to comply with all study procedures.

Exclusion Criteria

1. Concomitant use of any medication used to treat acid reflux.
2. Use of an investigational drug with in 30 days prior to enrollment.
3. Chronic PPI use.
4. PPI use 7 days prior to enrollment.
5. $H_2$ receptor antagonist use for 8 hours prior to enrollment.
6. Antacid use 4 hours prior to enrollment.
7. Pregnant or lactating female.
8. Dysphagia, or a feeling that food gets "stuck".
9. Diabetes.
10. Liver disease.
11. Allergies to any study medication
12. Allergies to cheese.
13. Use of any drug/herbal supplement in the five days or ten half-lives prior to Study Day 1 and Study Day 8 (whichever is longer) that is partially or completely metabolized by Cytochrome P450 2C19 or 3A4.
14. Use of any drug/herbal supplement in the past five days or ten half-lives (whichever is longer) that affects gastrin production.

Withdrawal/Early Termination Criteria

1. Participant withdraws consent.
2. Vomiting from probe placement that produces severe fluid losses (greater than 1.5 Liters)
3. Participant experiences a serious adverse event.

Treatment of Subjects

Concomitant medications. Concomitant use of the following will be prohibited: Any medication used to treat acid reflux will not be permitted during the study. The use of any drug/herbal supplement in the five days or ten half-lives before Study Day 1 and Study Day 8, (whichever is longer) that is partially or completely metabolized by Cytochrome P450 2C19 or 3A4. The use of any drug/herbal supplement in the five days or ten half-lives before Study Day 1 and Study Day 8, (whichever is longer) that affects gastrin production.

Treatments to be administered. Omeprazole 80 mg plus lansoprazole 80 mg power will be administered orally in the form of a suspension in 30 mL of water. It will be given once on Study day 1 or 8. Zegerid 40 mg powder will be also be administered orally as a suspension in 30 mL of water. It will be given once on Study day 1 or 8.

Treatment compliance. The procedure for monitoring treatment compliance will consist of the study staff observing the participant taking the study medication. The participant will be questioned by study staff on the use of prohibited medications.

Evaluation of Benefits and Risks/Discomforts/Adverse Events

Definition of adverse events. An adverse event is any untoward medical occurrence in a subject administered a pharmaceutical product. The AE does not necessarily have a causal relationship with the treatment. An AE can be any unfavorable and unintended sign, symptom, or disease temporarily associated with the use of a pharmaceutical product. A pre-existing condition is only considered an AE if there is an increase in frequency or severity or a change in nature or as a consequence of use of a medication in a clinical trial. Any AE with an onset date after consent and through study completion will be recorded in the CRF on the appropriate page.

An AE does not include:
Medical or surgical procedures; the condition that leads to the procedure is the AE
Pre-existing diseases or conditions present prior to consent.
Situations where an untoward medical occurrence has not occurred (e.g., hospitalization for elective surgery, social and/or convenience admissions)

Assessment of AEs. All AEs will be assessed by the investigators and recorded on the appropriate CRF page. Data recorded will include onset, resolution and outcome, severity, relationship to the study medication, and action taken.

Procedures for recording and reporting adverse events. AEs and SAEs will be reported to the IRB per the IRB policy. AEs and SAEs will be recorded in the Case Report Form binder.

Reasonably foreseeable risks and discomforts to the subjects. Study's foreseeable risks and discomforts of adverse events related to omeprazole contained in Zegerid are uncommon and mild. Adverse Events related to omeprazole and side effects related to lansoprazole and omeprazole are abdominal pain, asthenia, constipation, diarrhea and headache. Vomiting and/or gagging, coughing and aspiration of fluid into the lungs are possible adverse events of swallowing and withdrawing the Bravo pH probe. Possible adverse events of the tether are sore throat, superficial trauma to the oropharynx, intolerance and nausea. Possible adverse events of the tape used to secure the tether are skin rash and superficial skin trauma.

Procedures used to prevent and/or minimize any potential risks and discomfort. Participants will be monitored throughout the clinical phase of this study by study staff as follows:
- Participants will be monitored for signs and symptoms of allergic reaction to the test articles.
- Participants will be monitored for signs and symptoms of potential risks and discomfort potentially related to blood collection and the swallowing of the probe.
- Procedures/tests will be performed and explained by experienced staff.
- The tethering string will be used to reduce the risk of aspiration.

Appropriate personnel will be present when the participant swallows the Bravo pH probe and at withdraw the probe. Alternatively, the participant may choose to have the string cut. If resistance is met when withdrawing the probe, the string will be cut and appropriate personnel will be notified.

Potential benefits of participation for the subject. There may or may not be direct medical benefit to the participant. A participant may expect to benefit from taking part in this research to the extent that he/she is contributing to medical knowledge. We hope the information learned from this study will benefit other patients who require immediate control of acid secretion in the future.

The risk/benefit relationship for the participant in this project. The risk relative to benefit is minimal for two reasons: (1) PPI drugs are very specific in their mechanism of action as they are Pro-drugs that are only converted to their active form at a pH below 2. Since the only physiological location that satisfies this requirement is the parietal cell canalicular space, the effects of the drug are limited only to this area and (2) The subjects receive one dose of each drug separated by at least one week; therefore there is no chronic exposure risk. The possible benefit of taking part in this study is improving treatment for patients requiring immediate control of acid secretion.

Pregnancy

Pregnancy test administration. A urine pregnancy test will be administered to women of childbearing potential prior to acceptance into study and prior to the second dose of study drug in the second treatment period. Those testing positive will be excluded from the study. Lansoprazole is in pregnancy category B and Omeprazole and Zegerid are in category C. In studies of rats, lansoprazole or its metabolites were found to be excreted in breast milk. It is not known if Omeprazole is excreted into breast milk.

Birth control for women of child-bearing potential. Acceptable methods of birth control will be:
- Oral contraceptive
- Intra-uterine device
- Contraceptive injection, patch, or vaginal ring
- Double-barrier method; i.e. condom and spermicide
- Tubal ligation
- Male partner with a vasectomy
- Abstinence Assessment of Efficacy Specification of the efficacy parameters. The pH probe data will be used to determine integrated gastric acidity, an accepted measure of PPI efficacy, using the AcidipHy software.

Methods and timing for assessing, recording, and analyzing safety parameters. The goal of the blood draws is to characterize the pharmacokinetics of omeprazole and lansoprazole and the levels of Gastrin-17 in the participant's bloodstream. The concentration of omeprazole and lansoprazole in the participant's plasma will be determined and plotted on a concentration vs. time graph, which allows the determination of important pharmacokinetic parameters like elimination half-life ($t_{1/2}$), area under the curve of drug concentration (AUC), and maximum concentration ($C_{max}$). These parameters will give a good approximation of how much of the drug is in the participant's bloodstream and how long it stays there; therefore, an analysis can be made of when (and to what extent) the drug is most active in the participant.

The gastrin-17 assay will be conducted with each blood sample to determine the response of gastrin to the drug and to meals. Elevated gastrin concentrations are an indicator of increased activity of the parietal cells, which are the cells responsible for acid production in the stomach. The concentration of gastrin will be plotted on a separate graph with respect to time and will give an improved idea of how much stomach acid would normally be produced at any given time. The PPI inhibits the proton pumps and prevents the production of the acid, so the gastrin results (when combined with the pH) will help determine how effective the PPI is at suppressing the acid production.

It will be acceptable for blood draws to extend outside of scheduled times since characterization of pharmacokinetics can accommodate different times than scheduled if accurate time of blood draw is noted. Every effort will be made to adhere to the blood draw schedule.

Statistics

Statistical method. Statistical method to be used to analyze and compare data will be Student's T-test for paired data.

Power analysis. A 50% reduction in integrated acidity is expected on Day 1 when comparing: a single dose of Zegerid 40 mg to a single dose of omeprazole 80 mg plus lansoprazole 80 mg. The Power calculation results in a sample size per arm of 13 subjects, therefore a minimum of 26 subjects will be required for the full study. Enrollment of a total of 30 subjects will allow for drop-outs, of which 10% is expected. The calculation is based upon this formula $$n = \frac{S_1 \times (100 - S_1) + S_2 \times (100 - S_2)}{(S_2 - S_1)^2} \times f(\alpha, \beta)$$

|  |  | β (Type II error) | | | |
| --- | --- | --- | --- | --- | --- |
|  |  | 0.05 | 0.1 | 0.2 | 0.5 |
| α | 0.1 | 10.8 | 8.6 | 6.2 | 2.7 |
| (Type I error) | 0.05 | 13 | 10.5 | 7.9 | 3.8 |
|  | 0.02 | 15.8 | 15 | 10 | 5.4 |
|  | 0.01 | 17.8 | 14.9 | 11.7 | 6.6 |

Use the table above to calculate the $f(\alpha, \beta)$.

Choose an $\alpha$ and $\beta$ then cross reference.

Level of Significance. Level of significance to be used is $p<0.05$ alpha $p<0.2$ beta.

Procedure for accounting for missing or unused data. How and why the data was lost will be recorded. A calculation of pharmacokinetic parameters and integrated gastric acidity can proceed with some loss of data.

Participants to be included. The participants to be included in the analyses are healthy volunteers that complete the trial.

Study Costs

Costs that Will not be Paid by Participants or their Insurance Providers

Study Costs are Limited to:
All supplies needed for blood collection and all tests performed on the blood.
Study medications.
Bravo pH probe and associated monitor.
Breakfast and lunch meals.

Cost that will be paid by participants or their insurance providers. The participant will be required to pay for their transportation and parking and other travel costs. The use of other medications to help control side effects could result in added costs that may or may not be covered by participants' medical insurance. Upon completion of the trial, the participant will be paid up to the amount of $500. For the Study Day Minus visit they will receive $20. For each of the Study Days 1, 2, 8 and 9 visits they will receive $120. To receive the $120 at Study Days 1 and 8 the participant is required to make an effort to swallow the Bravo pH probe and if swallowed, to keep the probe in their stomach and to allow at least two attempts for insertion of an IV for blood draws. On Study Days 2 and 9 they are required to successfully complete the study procedures of the previous visits and to return the Bravo pH probe monitor. If the participant experiences and adverse event and cannot continue in the study they will receive compensation up through the visit day they experienced that adverse event.

Direct Access to Source/Data Documents

The investigator(s)/institution will permit trial-related monitoring, audits, IRB/IEC review, and regulatory inspection(s) by providing direct access to source data/documents. The FDA may also perform trial-related audits and will have direct access to all source data/documents.

Quality Control and Quality Assurance

Study medications will be purchased from the manufacturer and will be dispensed by appropriate personnel.

Compliance statement. This trial will be compliant with Good Clinical Practice and will meet all Institutional Review Board requirements.

Data safety monitoring plan. Study data will be reviewed after each group of participants, including a review of AEs for trends. The study staff will review the data and monitor the patients throughout the study and alert appropriate personnel if an adverse event is suspected. All adverse events will be reviewed by appropriate personnel. Appropriate personnel will be present when the participant swallows the Bravo pH probe and at withdraw the probe. If resistance is met, the string will be cut and appropriate personnel notified. Appropriate personnel will remain on call if complications arise while the participant is in an exam room. 911 will be used as back-up if they are unavailable. A crash cart will be available. Blood testing data will be analyzed. Test results and data files will be shared among those registered with the IRB as working on this study. All participant data and test results will be kept securely maintained at all times.

All references, including publications, patent applications, and patents, cited herein are hereby incorporated by reference to the same extent as if each reference there individually and specifically indicated to be incorporated by reference and were set forth in its entirety herein.

The use of the terms "a" and "an" and "the" and similar referents in the context of this disclosure (especially in the context of the following claims) are to be construed to cover both the singular and the plural, unless otherwise indicated herein or clearly contradicted by context. All methods described herein can be performed in any suitable order unless otherwise indicated herein or otherwise clearly contradicted by context. The use of any and all examples, or exemplary language (e.g., such as, preferred, preferably, particularly) provided herein, is intended merely to further illustrate the content of the disclosure and does not pose a limitation on the scope of the claims. No language in the specification should be construed as indicating any non-claimed element as essential to the practice of the claimed invention.

Alternative embodiments of the claimed invention are described herein, including the best mode known to the inventors for carrying out the claimed invention. Of these, variations of the disclosed embodiments will become apparent to those of ordinary skill in the art upon reading the foregoing disclosure. The inventors expect skilled artisans to employ such variations as appropriate, and the inventors intend for the claimed invention to be practiced otherwise than as specifically described herein.

Accordingly, the claimed invention includes all modifications and equivalents of the subject matter recited in the claims appended hereto as permitted by applicable law. Moreover, any combination of the above-described elements in all possible variations thereof is encompassed by the claimed invention unless otherwise indicated herein or otherwise clearly contradicted by context.

The use of individual numerical values are stated as approximations as though the values were preceded by the word "about" or "approximately." Similarly, the numerical values in the various ranges specified in this application, unless expressly indicated otherwise, are stated as approximations as though the minimum and maximum values within the stated ranges were both preceded by the word "about" or "approximately." In this manner, variations above and below the stated ranges can be used to achieve substantially the same results as values within the ranges. As used herein, the terms "about" and "approximately" when referring to a numerical value shall have their plain and ordinary meanings to a person of ordinary skill in the art to which the disclosed subject matter is most closely related or the art relevant to the range or element at issue. The amount of broadening from the strict numerical boundary depends upon many factors. For example, some of the factors which may be considered include the criticality of the element and/or the effect a given amount of variation will have on the performance of the claimed subject matter, as well as other considerations known to those of skill in the art. As used herein, the use of differing amounts of significant digits for different numerical values is not meant to limit how the use of the words "about" or "approximately" will serve to broaden a particular numerical value. Thus, as a general matter, "about" or "approximately" broaden the numerical value. Also, the disclosure of ranges is intended as a continuous range including every value between the minimum and maximum values plus the broadening of the range afforded by the use of the term "about" or "approximately." Thus, recitation of ranges of values herein are merely intended to serve as a shorthand method of referring individually to each separate value falling within the range, unless otherwise indicated herein, and each separate value is incorporated into the specification as if it there individually recited herein.

It is to be understood that any ranges, ratios and ranges of ratios that can be formed by, or derived from, any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art most closely related to a particular range, ratio or range of ratios will appreciate that such values are unambiguously derivable from the data presented herein.

What is claimed is:

1. A method of inhibiting gastric acid secretion comprising administering to a subject in need thereof a pharmaceutical composition comprising omeprazole in an amount of about 40 mg to about 120 mg, lansoprazole in an amount of about 40 mg to about 120 mg wherein the ratio of omeprazole to lansoprazole is 1:1, and at least one buffering agent in an amount of about 100 mg to about 4000 mg.

2. The method of claim 1, wherein the at least one buffering agent is selected from the group consisting of: sodium bicarbonate, calcium carbonate, calcium formate, magnesium hydroxide, aluminum, aluminum hydroxide/magnesium hydroxide co-precipitate, aluminum hydroxide/sodium bicarbonate co-precipitate, calcium acetate, calcium bicarbonate, calcium borate, calcium bicarbonate, calcium citrate, calcium gluconate, calcium glycerophosphate, calcium hydroxide, calcium lactate, calcium phthalate, calcium phosphates, calcium succinate, calcium tartrate, calcium propionate, dibasic sodium phosphate, dipotassium hydrogen thosphate, dipotassium phosphate, disodium hydrogen phosphate, disodium succinate, dry aluminum hydroxide gel, L-arginine, magnesium acetate, magnesium aluminate, magnesium borate, magnesium bicarbonate, magnesium carbonate, magnesium citrate, magnesium gluconate, magnesium lactate, magnesium metasilicate aluminate, magnesium oxide, magnesium phthalate, magnesium phosphate, magnesium silicate, magnesium succinate, magnesium tartrate, potassium acetate, potassium carbonate, potassium bicarbonate, potassium borate, potassium citrate, potassium metaphosphate, potassium phthalate, potassium phosphate, potassium polyphosphate, potassium pyrophosphate, potassium succinate, potassium tartrate, sodium acetate, sodium borate, sodium carbonate, sodium citrate, sodium gluconate, sodium hydrogen phosphate, sodium hydroxide, sodium lactate, sodium phthalate, sodium phosphate, sodium polyphosphate, sodium pyrophosphate, sodium sesquicarbonate, sodium succinate, sodium tartrate, sodium tripolyphosphate, synthetic hydrotalcite, tetrapotassium pyrophosphate, tetrasodium pyrophosphate, tripotassium phosphate, trisodium phosphate, trometamol, and mixtures of the foregoing.

3. The method of claim 1, wherein the at least one buffering agent comprises calcium carbonate and is present in an amount of about 400 mg to about 2500 mg.

4. The method of claim 1, wherein the at least one buffering agent comprises calcium formate and is present in an amount of about 400 mg to about 2500 mg.

5. The method of claim 1, wherein the at least one buffering agent comprises calcium carbonate and calcium formate.

6. The method of claim 5, wherein the calcium carbonate is present in an amount of about 300 mg to about 3000 mg and the calcium formate is present in an amount of about 100 mg to about 4000 mg.

7. The method of claim 1, further comprising one or more pharmaceutically acceptable excipients.

8. The method of claim 7, wherein the one or more pharmaceutically acceptable excipient is selected from the group consisting of: diluents, disintegrants, binding agents, adhesives, wetting agents, lubricants, glidants, surface modifying agents, substances added to mask or counteract a disagreeable taste or odor, flavors, dyes, fragrances, and substances added to improve appearance of the composition.

9. The method of claim 8, wherein the disintegrant is selected from the group consisting of: croscarmellose sodium and sodium carboxymethylcellulose.

10. The method of claim 8, wherein the lubricant is magnesium stearate.

11. The method of claim 1 wherein the composition is present in one or more discrete dosage units.

12. The method of claim 11, wherein the one or more discrete dosage units are selected from tablets, caplets, capsules, powder, lozenges, sachets, cachets, troches, pellets, granules, solutions, suspensions, elixers, syrups, liquid aerosol formulations and mixtures thereof.

13. The method of claim 1 wherein the lansoprazole is present in an amount of about 50 mg to about 150 mg.

14. The method of claim 1 wherein the omeprazole is present in an amount of about 70 mg to about 100 mg and the lansoprazole is present in an amount of about 70 mg to about 100 mg.

15. The method of claim 1 wherein the buffering agent comprises sodium bicarbonate.

16. The method of claim 1 wherein the buffering agent comprises sodium bicarbonate, calcium carbonate and/or calcium formate.

17. The method of claim 11 wherein the composition is administered to the subject daily for a period effective to treat said disease or disorder.

18. The method of claim 1, wherein said subject has a gastric acid disease or disorder selected from the group consisting of severe erosive esophagitis (Los Angeles classification grade C & D), Barrett's esophagus, reflux-related esophageal metaplasia with low or high grade dysplasia, reflux-related adenocarcinoma of the esophagus, acid-related adenocarcinoma of the stomach, duodenal ulcer, gastric ulcer, gastric and duodenal erosions and ulcerations, acid dyspepsia, gastroesophageal reflux disease (GERD), poorly responsive symptomatic GERD, acid reflux, esophageal ulcers and erosions, precancerous and cancerous lesions of the esophagus induced by acid exposure, radiation- or chemotherapy-induced esophagitis, acid hypersecretory conditions, gastrointestinal pathological hypersecretory conditions, Zollinger Ellison Syndrome, non-ulcer dyspepsia, short-term eradication of *Helicobacter pylori* (*H. pylori*), extraesophageal or atypical manifestations of gastroesophageal reflux disease, nocturnal acid breakthrough (NAB), sleep apnea, sleep disturbance, gastrointestinal bleeding, rebleeding after gastrointestinal bleeding, stress ulcer prevention, stress-related bleeding, seizure or apparent seizure activity, Sandifer's syndrome, failure to thrive, anorexia, anorexia nervosa, weight loss, apnea, and bradycardia.

19. The method of claim 1, wherein the subject has gastroparesis.

20. The method of claim 1, wherein the subject does not have gastroparesis.

21. The method of claim 18, wherein the extraesophageal or atypical manifestations of gastroesophageal reflux disease are selected from the group consisting of eye pain, asthma, bronchitis, pneumonia, chest pain, cough, recurrent laryngitis, globus pharyngeus, sinusitis, otalgia, otitis media, eustachian tube dysfunction, voice change, globus sensation, throat clearing, halitosis, sore throat, and aphthous ulcers.

22. The method of claim 1, wherein the pharmaceutical composition is administered prior to endoscopic evaluation of upper GI bleeding.

23. The method of claim 18, wherein the gastric acid-related disease or disorder comprises extraesophageal or atypical manifestations of gastroesophageal reflux disease.

24. A method of treating extraesophageal or atypical manifestations of gastroesophageal reflux disease in a subject in need thereof, comprising administering to a subject a pharmaceutical composition comprising about 40 mg to about 120 mg of omeprazole, about 40 mg to about 120 mg of lausoprazole, about 400 mg of calcium formate, and about 1680 mg of sodium bicarbonate wherein the ratio of omeprazole to lansoprazole is 1:1.

25. A method of inhibiting gastric acid secretion comprising administering to a subject in need thereof a pharmaceutical composition comprising about 80 mg of omeprazole, about 80 mg of lansoprazole, about 400 mg of calcium formate, and about 1680 mg of sodium bicarbonate, wherein the composition is provided in one or two dosage units.

26. The method of claim 25 wherein wherein said subject has extraesophageal or atypical manifestations of gastroesophageal reflux disease.

\* \* \* \* \*